United States Patent
Tran

(10) Patent No.: US 9,410,907 B2
(45) Date of Patent: Aug. 9, 2016

(54) METHODS AND APPARATUSES FOR TESTING CAPACITIVE TOUCH SCREEN FILMS

(71) Applicant: Clarus Vision, Inc., Austin, TX (US)

(72) Inventor: Khanh Ngoc Tran, Austin, TX (US)

(73) Assignee: Clarus Vision, Inc., Austin, TX (US)

( * ) Notice: Subject to any disclaimer, the term of this patent is extended or adjusted under 35 U.S.C. 154(b) by 281 days.

(21) Appl. No.: 14/134,663

(22) Filed: Dec. 19, 2013

(65) Prior Publication Data

US 2015/0177314 A1 Jun. 25, 2015

(51) Int. Cl.
*G01N 27/02* (2006.01)
*G06F 3/044* (2006.01)

(52) U.S. Cl.
CPC .............. *G01N 27/02* (2013.01); *G06F 3/044* (2013.01)

(58) Field of Classification Search
USPC .................... 324/658, 537, 686, 691, 750.02, 324/750.19, 756.01, 756.05, 760.01, 324/762.07; 345/174, 173, 177, 178; 29/825, 846, 593, 832; 361/280, 809; 702/104, 121, 65; 200/600; 327/517
See application file for complete search history.

(56) References Cited

U.S. PATENT DOCUMENTS

| | | | | |
|---|---|---|---|---|
| 6,885,205 B2 * | 4/2005 | Siew | ................. | G01R 31/2806 324/754.16 |
| 6,977,646 B1 * | 12/2005 | Hauck | ................. | G06F 3/0418 345/173 |
| 6,980,201 B1 * | 12/2005 | Dotson | ................. | G06F 3/0383 178/18.01 |
| 8,253,425 B2 | 8/2012 | Reynolds et al. | ............. | 324/658 |
| 8,279,197 B2 | 10/2012 | Murphy et al. | ............... | 345/174 |
| 2002/0028456 A1 * | 3/2002 | Mansky | ............... | B01J 19/0046 435/6.19 |
| 2008/0278453 A1 | 11/2008 | Reynolds et al. | ............. | 345/173 |
| 2012/0268413 A1 | 10/2012 | Narasimhan et al. | .......... | 345/174 |
| 2013/0057509 A1 * | 3/2013 | Cruz-Hernandez | ..... | G06F 3/016 345/174 |
| 2013/0278539 A1 | 10/2013 | Valentine et al. | ............. | 345/174 |

FOREIGN PATENT DOCUMENTS

| | | | |
|---|---|---|---|
| CN | 202793443 | 3/2013 | |
| CN | 103018594 | 4/2013 | |
| EP | 1754976 | 9/2010 | |
| JP | 05127807 A * | 5/1993 | ................ G06F 3/03 |

(Continued)

OTHER PUBLICATIONS

JP-05127807 A , Tajima Masaya et al., Touch coordinate input device, May 25, 1993, 20 pages, JP, Fujitsu Ltd.*

(Continued)

*Primary Examiner* — Melissa Koval
*Assistant Examiner* — Nasima Monsur
(74) *Attorney, Agent, or Firm* — Norton Rose Fulbright US LLP

(57) ABSTRACT

Test fixtures for testing layers of touch screen material and methods for using the same. Some test fixtures include first and second test beds that are movable relative to each other, an impedance measurement circuit, an electrical connector, a clamping actuator, and a processor, where the test fixtures and/or test fixture components are configured to secure a layer of touch screen material and measure the electrical impedance of at least one feature of the layer. Some of the present methods include securing a layer of touch screen material between test beds, calculating an electrical impedance of at least one feature of the layer, and releasing the layer from the test beds.

20 Claims, 13 Drawing Sheets

(56) References Cited

FOREIGN PATENT DOCUMENTS

| WO | WO 2010/057059 | 5/2010 |
|---|---|---|
| WO | WO 2011/021825 | 2/2011 |

OTHER PUBLICATIONS

International Search Report and Written Opinion for PCT/US2014/071195 mailed Mar. 26, 2015.

John V. of PhoneArena.com, "Automated Touchscreen Test Device Shows Off the Accuracy of Smartphones" Mar. 26, 2010 <http://www.phonearena.com/news/Automated-touchscreen-test-device-shows-off-the-accuracy-of-smartphones_id10418> accessed Apr. 4, 2014.

K-9604 Capacitive TSP Module Test Equipment.

OpenInnobiz.com, "Capacitive Touch Panel testing system" product specifications. <http://www.openinnobiz.com/html/products/selling_view.asp?no=297> accessed Apr. 4, 2014.

PR Newswire, "Synaptics Introduces Capacitive Touch Screen Testing Application" Oct. 4, 2012 <http://www.prnewswire.cominews-releases/synaptics-introduces-capacitive-touch-screen-testing-application-172644061.html> accessed Apr. 4, 2014.

Richardson, Jeffrey Lee, "A Systematic Approach to Verify an Embedded Capacitive Touchscreen System" Master's Thesis at Boise State University, Aug. 2013.

Texas Instruments "TouchPath TM Capacitive Touch Screen Controller" Nov. 2012, revised Jan. 2013.

TouchInternational.com, "Test for Touch with the Projected Capacitive Test Fixture from Touch International" Mar. 16, 2010 <http://touchinternational.com/news/press-031610.html>, accessed Apr. 4, 2014.

* cited by examiner

METHODS AND APPARATUSES FOR TESTING CAPACITIVE TOUCH SCREEN FILMS

BACKGROUND

1. Field of Invention

The present invention relates generally to touch screen sensor manufacturing, and more specifically, but not by way of limitation, to testing layers of touch screen material before integration into completed touch screen sensors.

2. Background of the Invention

Touch-sensitive input allows a user to interact directly with a device, as opposed to indirectly through traditional input devices such as keyboards or mice. Due to the intuitive user experience or the smaller form factor provided by the lack of need of additional input peripherals, more and more devices are employing touch-sensitive input. From industrial to recreational devices, touch screens have become ubiquitous. As technology expands, the universe of devices that employ touch sensitive input will likewise grow.

Touch screen sensors are generally transparent and mounted in front of a display device (such as an LED display). In general, a user seeks to touch an object on the display. The touch sensor registers the location of the touch and communicates with the device to perform an action, for example, starting an application, following a link, or performing a specified function. In this way, even complex computing tasks can be performed with only a single finger touch. Current touch screen sensors work by using various electrical and mechanical properties. The two major types of touch screen sensors are resistive and capacitive touch screens. The construction of both types of sensors generally relies on transparent insulating sheets that are printed with thin or transparent materials that have specified electrical properties. For example, resistive touch screens are generally constructed from at least two thin sheets printed with a resistive material. The two sheets are separated by a small and substantially hollow air gap and during operation one layer is provided with a voltage. When a user or an object presses on one of the layers, the layers mechanically deform and connect at a location that can be determined by a processor. Because such sensors necessarily rely on mechanical deformation, resistive touch sensors tend to wear out or are prone to damage from sharp objects. Capacitive touch screens, on the other hand, are the majority of touch screen sensors and do not rely on mechanical deformation. These sensors are generally constructed out of a thin sheet of insulating material (that can be two or more sheets bonded together) coated with thin, semi-transparent or transparent electrodes. The electrodes are generally printed in rows on one side of the sheet and columns on the other side to define junctions where the rows and columns cross over one another. These are generally known as projected capacitance touch screen sensors. When an electrically conductive object, such as a human finger, nears or touches the surface, a distortion in the electrostatic field creates a change in the capacitance of the system at nearby junctions which can be monitored by a processor to determine a touch location. Capacitive touch screen sensors generally come in two types: self-capacitance and mutual capacitance. Self-capacitance sensors, in operation, monitor the capacitive load on each column and row electrode by measuring the current through each column and row electrode. Alternatively, mutual capacitance sensors, in operation, are capable of monitoring the capacitance at each point on the sensor, generally, by measuring the capacitance at each junction. Mutual capacitance sensors produce a weaker signal than self-capacitance sensors, but are capable of accurately tracking multiple touch inputs.

As described above, the majority of touch screen sensors, including resistive, self-capacitive, and mutual capacitive sensors, employ layers (constructed out of thin sheets) with printed semi-transparent or transparent features with specified electrical or mechanical properties (touch screen circuit patterns). These layers are often provided to a touch screen sensor manufacturer on rolls (with touch screen circuit patterns already printed). The layers can then be integrated into the completed touch screen sensor, for example, by bonding a layer to a piece of glass and coupling the layer to a processor. Because layers of touch screen material must be semi-transparent (to allow images from the underlying display to reach the user), layer construction is a delicate process. For example, electrodes in a typical mutual capacitive touch sensor are generally printed on a thin sheet of insulating material, such as polyethylene terephthalate (PET), using iridium tin oxide (ITO) or silver. These electrodes are so small that they usually cannot be seen by the naked eye. Therefore, construction of such layers is particularly susceptible to manufacturing defects. Typically, touch screen sensors are tested once they are completed. A common approach involves an operator moving their finger around the completed touch screen sensor in a set pattern. If any defective layer features are present, touch inputs may be ignored or erroneous touch inputs may be received. Not only is this approach prone to operator error and time consuming, it also requires the touch sensor to be completed. If the layer of touch screen material itself is defective, the materials and time required to assemble the sensor will have been wasted.

Therefore, it is advantageous to provide a test fixture for testing of layers of touch screen material. Through such features, defective layers of touch screen material can be detected before the touch screen sensors are completed and materials are wasted. Additionally, touch screen sensor testing time can be significantly reduced. Due to the wide variety of touch screen sensors currently available, it is also advantageous to provide a test fixture that is capable of testing a variety of types of touch screen materials (e.g., with various touch screen circuit patterns) through quick and modular test fixture configuration changes.

SUMMARY

Disclosed is a test fixture for testing a layer of capacitive touch screen material having terminals coupled to capacitive junctions, the test fixture comprising including first and second test beds moveable relative to each other, at least one test bed including an impedance measurement circuit coupled to at least one electrical connector, at least one clamping actuator configured to move at least one test bed relative to the other test bed to secure a layer of capacitive touch screen material having terminals coupled to capacitive junctions between the first and second test beds and to place the at least one electrical connector in electrical contact with the terminals, the impedance measurement circuit being operable to test an electrical impedance of at least one junction of the layer when the layer is secured between the test beds. The impedance measurement circuit may include a processor programmed to determine impedance.

The test fixture of may further comprise at least one orientation actuator configured to move at least one test bed in at least one of a transverse or rotational degree of freedom relative to the layer, and at least one test bed may include a spacer configured to prevent contact with the junctions of the layer when the layer is secured between the test beds, with the spacer having an aperture configured to secure an electrical connector and substantially restrain the electrical connector from laterally deflecting when the layer is secured between the test beds. The electrical connector may be an elastomeric electrical connector. The fixture may further include a sensor, for example a camera, configured to capture data indicative of the orientation of the layer relative to the test fixture and to control the orientation actuator to align the test fixture with the layer.

One of the test beds may include a spacer of a conductive material configured to contact the junctions of the layer when the layer is secured between the test beds. Further, the fixture may be configured to include apparatus configured to allow removal and replacement of at least one test bed; and at least one latch configured to releasably secure the at least one test bed within the test fixture.

Other embodiments of the disclosure include a method for testing a layer of capacitive touch screen material having terminals coupled to capacitive junctions, comprising, securing the layer between first and second test beds, at least one test bed having an impedance measurement circuit and an electrical connector, such that the terminals are in electrical contact with the electrical connector of the at least one test bed, calculating an electrical impedance of at least one junction of the layer; and releasing the layer from the test beds. The method may further comprise monitoring an orientation of the layer relative to the electrical connector of the at least one test bed, with the monitoring including locating a position of a first fiducial disposed on the layer, locating a position of a second fiducial disposed on the test fixture, and comparing the positions of the first and second fiducials, and then adjusting an orientation of at least one test bed relative to the layer based on the comparison of the positions of the first and second fiducials. Further, the advancement of the layer may be controlled based on the comparison of the positions of the first and second fiducials.

When the junctions of the layer are defined by a plurality of elongated drive and sense electrodes, the calculation of electrical impedance step may include selecting a first drive electrode of the layer; applying an alternating current signal to the first drive electrode, selecting a first sense electrode, measuring a responsive signal corresponding to the junction defined by the first drive electrode and the first sense electrode, calculating an electrical impedance of the junction based on the responsive signal, repeating steps of selecting drive and sense electrodes until each drive and sense electrode has been selected The method may further include marking the layer based on the electrical impedance of the at least one junction of the layer, and may include storing, in a memory, data indicative of the electrical impedance of the at least one junction of the layer.

Another embodiment of the disclosure is a test bed for testing a layer of capacitive touch screen material, including a measurement circuit and a connector, the measurement circuit configured to be in electrical contact with a layer of a capacitive touch screen material via the connector, the layer having terminals coupled to capacitive junctions; and a spacer configured to be disposed between the test bed and the layer such that the test bed does not contact the capacitive junctions of the layer when the measurement circuit is in electrical contact with the layer. The spacer may be configured such that the connector passes through the spacer, the connector being secured by the spacer and substantially restrained from laterally deflecting under compression.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, 10, and 20 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, an apparatus that "comprises," "has," "includes," or "contains" one or more elements possesses those one or more elements, but is not limited to possessing only those elements. Likewise, a method that "comprises," "has," "includes," or "contains" one or more steps possesses those one or more steps, but is not limited to possessing only those one or more steps.

The feature or features of one embodiment may be applied to other embodiments, even though not described or illustrated, unless expressly prohibited by this disclosure or the nature of the embodiments. Some details associated with the embodiments are described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

DETAILED DESCRIPTION

Figure 1:
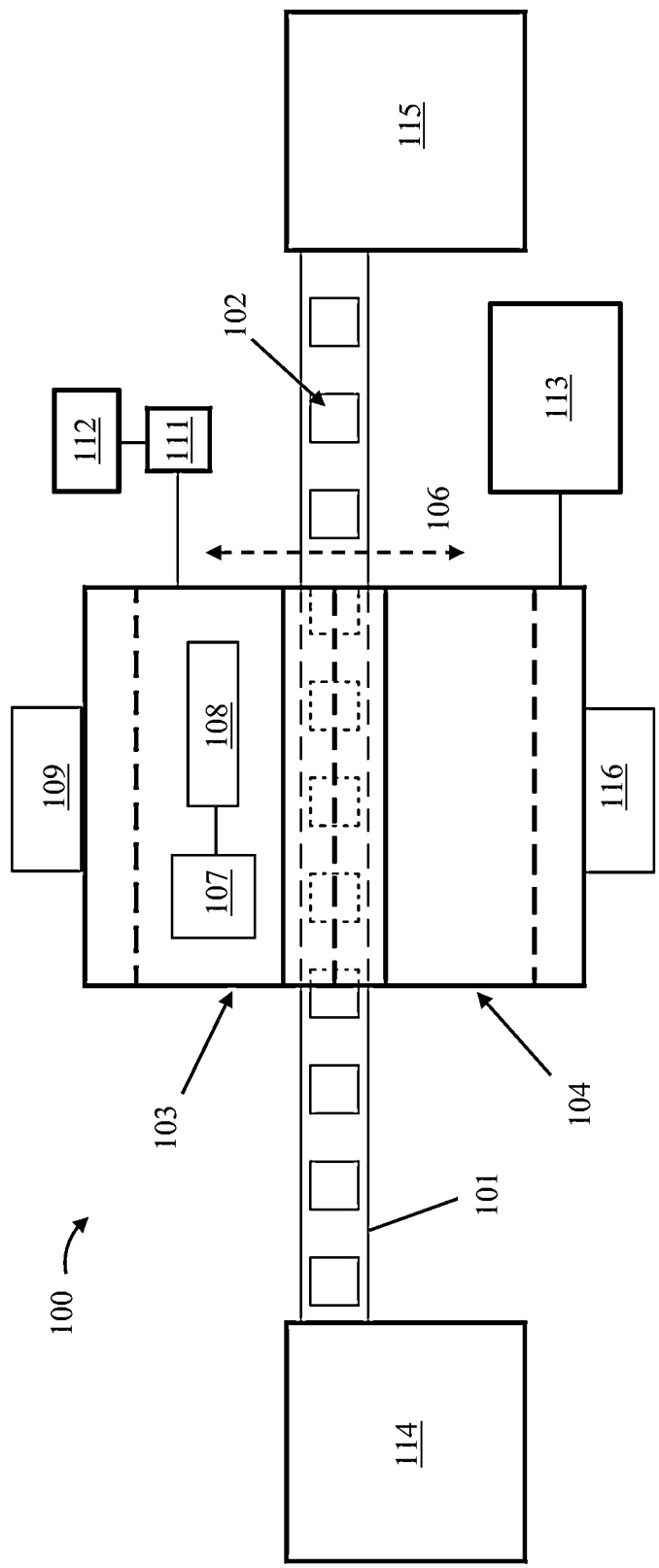
FIG. 1 is a conceptual block diagram of one embodiment of the present test fixtures.

FIG. 1 is a conceptual block diagram of embodiment 100 of the present test fixtures. In the embodiment shown, test fixture 100 is configured to test a mutual capacitive layer of touch screen material 101 with touch screen circuit patterns 102 having terminals coupled to capacitive junctions. In the embodiment shown, test fixture 100 comprises first and second test beds 103, 104 which are movable relative to each other, for example, in the direction indicated by arrow 106. In the embodiment shown, at least one test bed 103, 104 comprises an impedance measurement circuit 107 (described in more detail below) coupled to at least one electrical connector 108. Test fixture 100 further comprises at least one clamping actuator 109 configured to move at least one test bed 103, 104 relative to the other to secure layer of touch screen material 101. In the embodiment shown, the layer of touch screen material 101 comprises touch screen circuit patterns 102 having terminals coupled to capacitive junctions and the test beds 103, 104 are configured to secure the layer such that the at least one electrical connector 108 is in electrical contact with the terminals. Impedance measurement circuit 107 is thus operable to test an electrical impedance of at least one capacitive junction of the layer of touch screen material secured between the first and second test beds (described in more detail below). In the embodiment shown, test fixture 100 further comprises a processor 111 programmed to calculate the electrical impedance. In some embodiments, processor 111 may be located within impedance measurement circuit 107, or processor 111 may be outside the impedance measurement circuit and disposed on or within test fixture 100, for example, disposed on or within test bed 103 and/or test bed 104. In yet other embodiments, processor 111 is not a component supplied with or mounted on the present test fixtures but is a separate component. Unless otherwise indicated by the context of its use, the terms "a processor" or "the processor" mean one or more processors and may include multiple processors configured to work together to perform a function. In the embodiment shown, test fixture 100 further comprises memory 112 which may be configured to receive data from processor 111 and/or impedance measurement circuit 107 indicative of the impedance of at least one capacitive junction of the layer of touch screen material (for example, to detect if a capacitive junction of the layer is shorted or broken). Memory 112 may also be configured to store other information, such as any serial number(s) on the layer of touch screen material and/or the test date, as well as information regarding the test fixture (for example, number of tests run, errors, and/or the like). Through such features, data stored in memory 112 may additionally be used for troubleshooting (e.g., by reading any error code(s) stored in memory 112). In the embodiment shown, test fixture 100 may further comprise a user interface 113, which may include, for example, a computer and/or a touch-screen monitor coupled to processor 111 and/or impedance measurement circuit 107. User interface 113 may be configured to allow user control of test fixture 100 (e.g., starting and stopping the test fixture, manual testing of layers of touch screen material 101, and/or the like), as well as display information to a user (for example, test information regarding a layer of touch screen material, including, but not limited to, test date, layer and/or circuit pattern serial number, pass, fail, and/or the like, as well as regarding the operation of the test fixture itself, such as hardware failures, software failures, and/or the like). Such configuration of user interface 113 may be accomplished through a graphical user interface (GUI) (e.g., provided by software) on a computer which may be connected to and/or in control of the test beds and/or the test fixture (for example, in control of any orientation actuator(s) 116 (introduced below), clamping actuator(s) 109, processor(s) 111, impedance measurement circuit(s) 107 or the like). In some embodiments, processor 111 may perform many or all of the control functions and relay information to user interface 113 (e.g., as opposed to using a separate computer).

Also shown in FIG. 1 are output roller 114 and uptake roller 115. Test fixture 100, as with many embodiments of the present test fixtures, is configured to accept a layer of touch screen material 101 from an output roller 114. Through such features, test fixture 100 is able to receive an unrolled portion of a layer of touch screen material, test touch screen circuit patterns 102 of the layer 101, and pass the layer to an uptake roller 115, which can then re-roll the layer of touch screen material for easy storage, transport, and/or for use in later manufacturing of touch screen sensors. In some of these embodiments, processor 111 may further be configured to communicate with rollers 114, 115 to control the rate of advance of the layer of touch screen material 101 through the test fixture 100.

It should be noted that while rollers 114, 115 are shown in FIG. 1, other types of material handling apparatus may also be used. For example, touch screen material 101 may be supplied in the form of sheets with one or more touch screen circuit patterns 102 printed on each sheet, and in that case output roller 114 would be replaced with a sheet feed apparatus, and uptake roller 115 would be replaced with a sheet stacking apparatus. Also, rather than storing tested touch screen material 101 on uptake roller 115, tested material 101 may be supplied to another touch screen assembly apparatus, for example, a cutter or a laminator.

In the embodiment shown, test fixture 100 may further comprise at least one orientation actuator 116 (structure and operation described in more detail below) configured to move at least one test bed 103, 104 in at least one of a transverse or rotational degree of freedom relative to the layer 101, for example, to ensure proper alignment between the test fixture 100 and the layer of touch screen material 101 before test beds 103 and 104 are clamped together by clamping actuator 109 for testing.

Figure 2A:
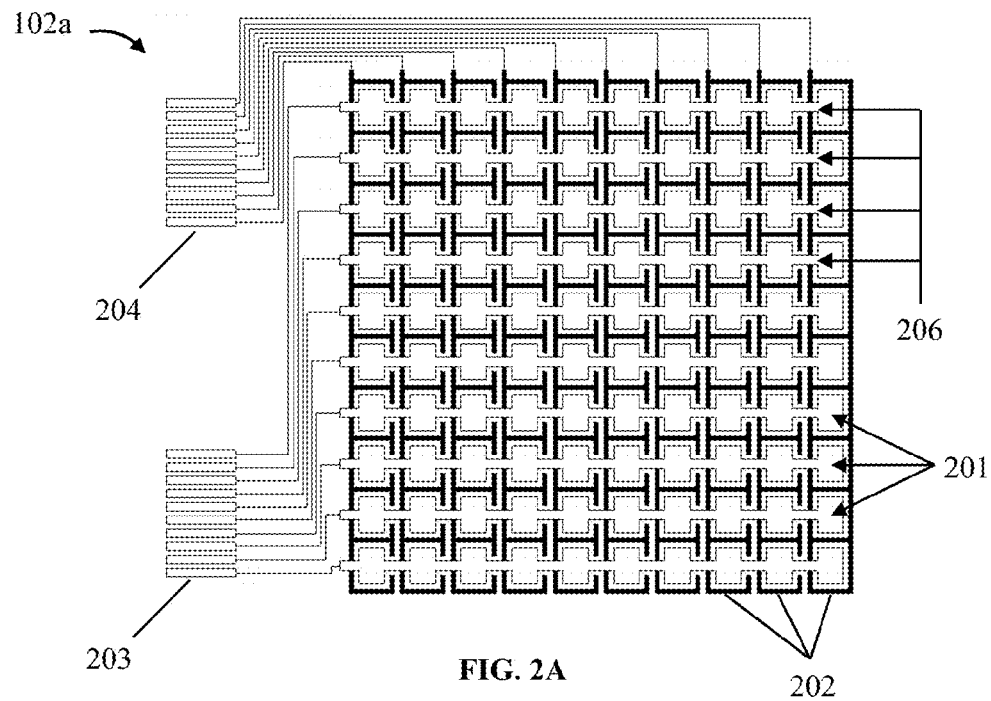
FIG. 2A is a touch screen circuit pattern for a single-sided mutual capacitive layer of touch screen material printed on one side of a layer.
Figure 2B:
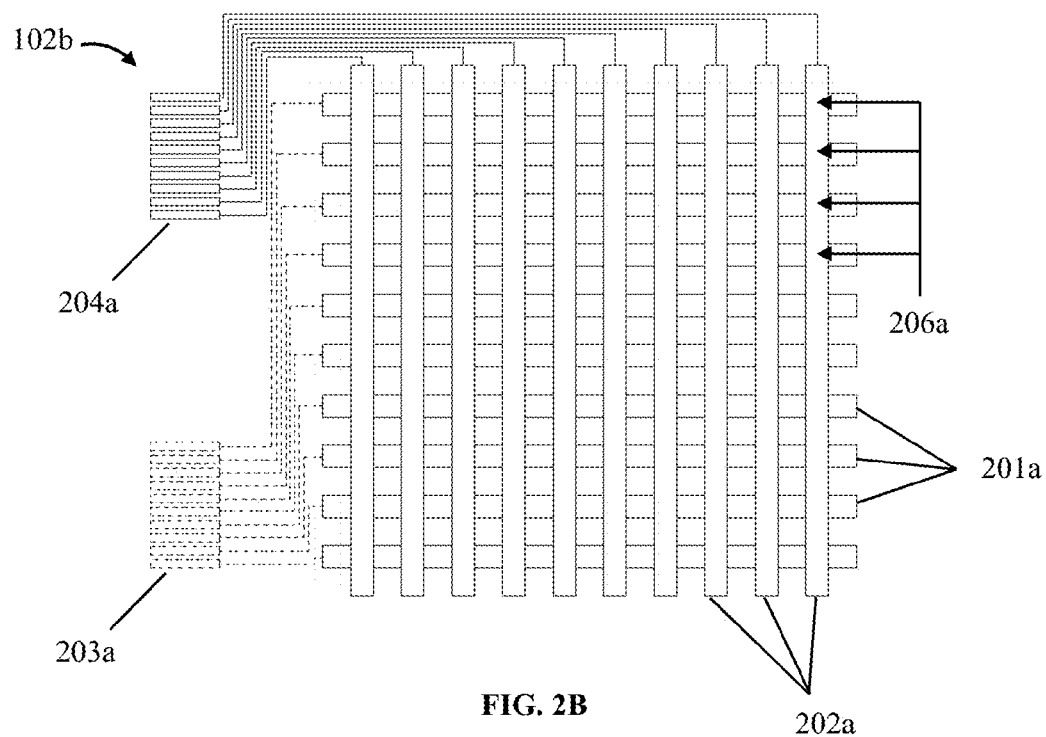
FIG. 2B is a touch screen circuit pattern for a two-sided mutual capacitive layer of touch screen material printed on both sides of a layer.

FIG. 2A is a single-sided mutual capacitance circuit pattern 102a that may be disposed on a sheet of material to form a single-sided mutual capacitive layer of touch screen material 101. Generally, such capacitive layers of touch screen material are comprised of a sheet of transparent and insulating material, for example, PET with rows and columns of printed drive and sense electrodes 201 and 202, respectively, connected to corresponding printed terminals 203 and 204, respectively. Capacitive junctions 206 are defined by the locations where the row and column electrodes cross over one another. During operation, an alternating current (AC) signal is applied iteratively to each of drive electrodes 201. Due to capacitive coupling, a responsive signal is generated within the sense electrodes 202, which can be measured, for example, from sense terminals 204, to determine the capacitance at a given junction. When an object nears or touches a mutual capacitive touch screen sensor, the electrostatic field in the vicinity of the object is distorted, which can be measured as a change in capacitance at nearby junctions (e.g., 206) to determine the touch location. FIG. 2B is a two-sided mutual capacitance circuit pattern 102b that may be disposed on sheet(s) of material to form a two-sided mutual capacitive layer of touch screen material 101. Touch screen circuit pattern 102b is substantially similar to 102a, with the primary exception that one set of electrodes, for example, drive electrodes 201a or sense electrodes 202a, and corresponding terminals, for example, drive terminals 203a or sense terminals 204a, are disposed on an opposite side of the layer from the other set of electrodes and terminals. Due to the two-sided nature of such mutual capacitive layers of touch screen material, such layers are generally constructed out of two sheets, for example, one sheet containing the drive electrodes 201a and drive terminals 203a, the other sheet containing the sense electrodes 202a and sense terminals 204a, where the sheets are bonded together to form a two-sided mutual capacitive layer of touch screen material (e.g., comprising two-sided mutual capacitive touch screen circuit pattern 102b). If such mutual capacitive layers of touch screen material are defective, for example, if the electrodes and/or junctions are shorted, broken, and/or printed too thinly, completed sensors may suffer from erroneous and/or ignored touch inputs.

Figure 3:
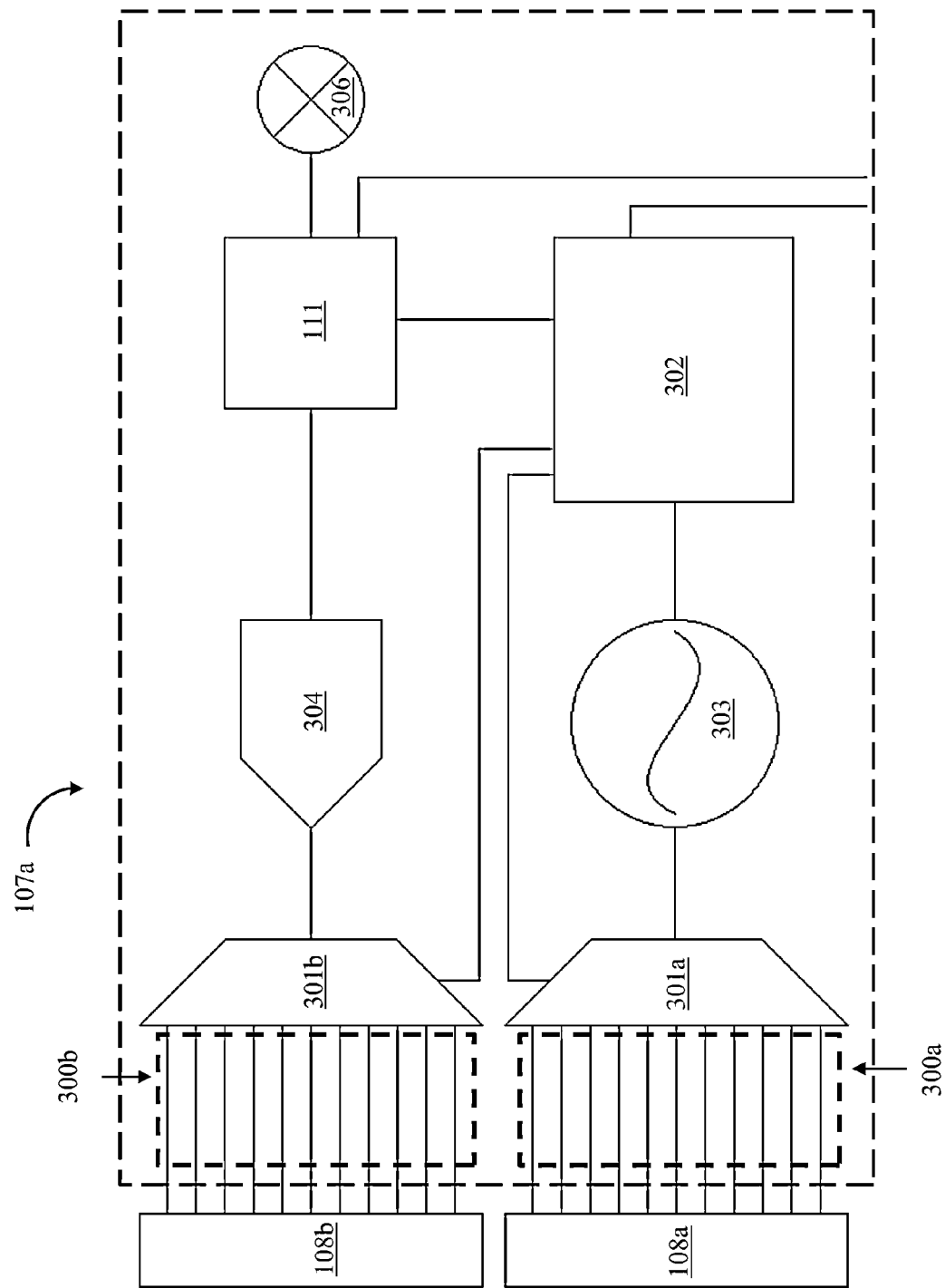
FIG. 3 is an example of impedance measurement circuit(s) of embodiments of the present test fixtures configured to test the mutual capacitive layers of touch screen material of FIGS. 2A and 2B.

FIG. 3 is impedance measurement circuit(s) of one embodiment of the present test fixtures configured to test a single-sided mutual capacitive layer of touch screen material 101 including touch screen circuit pattern 102. As described in more detail below, embodiments of the present test fixtures are configured to measure a variety of types layers of touch screen material 101 which comprise a variety of touch screen circuit patterns 102. Therefore the configuration of test beds 103, 104, the configuration and number of impedance measurement circuits 107, and/or the configuration and number of electrical connectors 108 may vary to accommodate the various touch screen circuit patterns of various layers of touch screen material, for example, through removal and replacement of modular test beds 103 and/or 104 of the test fixtures, described in more detail below. For example, in the embodiment shown, impedance measurement circuit 107a may be configured to test the electrical impedance of at least one capacitive junction (for example junction 206) within mutual capacitive touch screen circuit pattern 102a of a mutual capacitive layer of touch screen material 101. In this embodiment, impedance measurement circuit 107a comprises circuitry 300a, 300b in electrical communication with electrical connectors 108a, 108b, respectively. However, in other embodiments configured to test the same single-sided mutual capacitive layer of touch screen material, electrical connectors 108a, 108b may be a single electrical connector. In the embodiment shown, circuitry 300a is configured to place a first multiplexer 301a into electrical communication with connector 108a, and thus selectively drive terminals 203 and corresponding drive electrodes 201, for example, when test bed 103 is moved relative to test bed 104 to secure the layer 101. Multiplexer 301a may be configured to select, for example, through electrical communication with control unit 302, individual drive terminals 203 and corresponding drive electrodes 201 of the layer 101 such that alternating current (AC) signal generator 303 supplies an alternating current signal to the individually addressable drive terminals 203 and thus drive electrodes 201. Through capacitive coupling, a responsive signal can be generated within the sense electrodes 202 of the layer 101. In the embodiment shown, circuitry 300b is configured to place a second multiplexer 301b into electrical communication with electrical connector 108b and thus the sense terminals 204 and corresponding sense electrodes 202 of the single-sided mutual capacitive layer of touch screen material, for example, when test bed 103 moves relative to test bed 104 to secure the layer. Multiplexer 301b may be configured to select, for example, through electrical communication with control unit 302, individual sense terminals 204 and corresponding sense electrodes 202 of the layer 101. A responsive signal from each sense electrode 202 for each drive electrode 201 receiving an AC signal may be passed through an analog to digital converter (ADC) 304 and converted into digital form where it may be received by processor 111 shown within impedance measurement circuit 107a. In other embodiments, as described above for test fixture 100, processor 111 may be located outside of the impedance measurement circuit, and in yet other embodiments, processor 111 may be an integral part of control unit 302, for example, located within control unit 302. In the embodiment shown, processor 111 is programmed to communicate with control unit 302 to select individually addressable drive and sense electrodes 201, 202 and to measure the electrical impedance of at least one of the capacitive junctions 206 of the single-sided mutual capacitive layer of touch screen material 101. In the embodiment shown, processor 111 is further configured to activate an indicator 306 based on the measured electrical impedance of the at least one of the capacitive junctions. Indicator 306 may comprise, for example, a display, light and/or a speaker, and/or the like. For example, processor 111 may activate indicator 306 if the impedance of the at least one of the capacitive junctions 206 indicates a fault, for example, capacitance out of specification, shorted, broken, and/or the like. Impedance measurement circuits 107 in other like embodiments may comprise only circuitry 300b and/or 300a, and other components, for example, first multiplexer 301a, second multiplexer 301b, AC signal generator 303, ADC 304, control unit 302, processor 111, and/or indicator 306, may be located outside of the impedance measurement circuit or outside of the test fixture. Test fixtures configured to test single-sided mutual capacitive layers of touch screen material, for example, comprising single-sided mutual capacitive touch screen circuit pattern 102b, may be substantially similar, with the primary exception that such embodiments comprise two test beds (for example, 103 and 104, where each test bed comprises a connector 108 and an impedance measurement circuit 107, such that the test fixtures may communicate with both drive terminals 203a and sense terminals 204a that are disposed on opposite sides of the layer 101. The components within such impedance measurement circuits may be substantially identical to impedance measurement circuit 107a described above.

Figure 4:
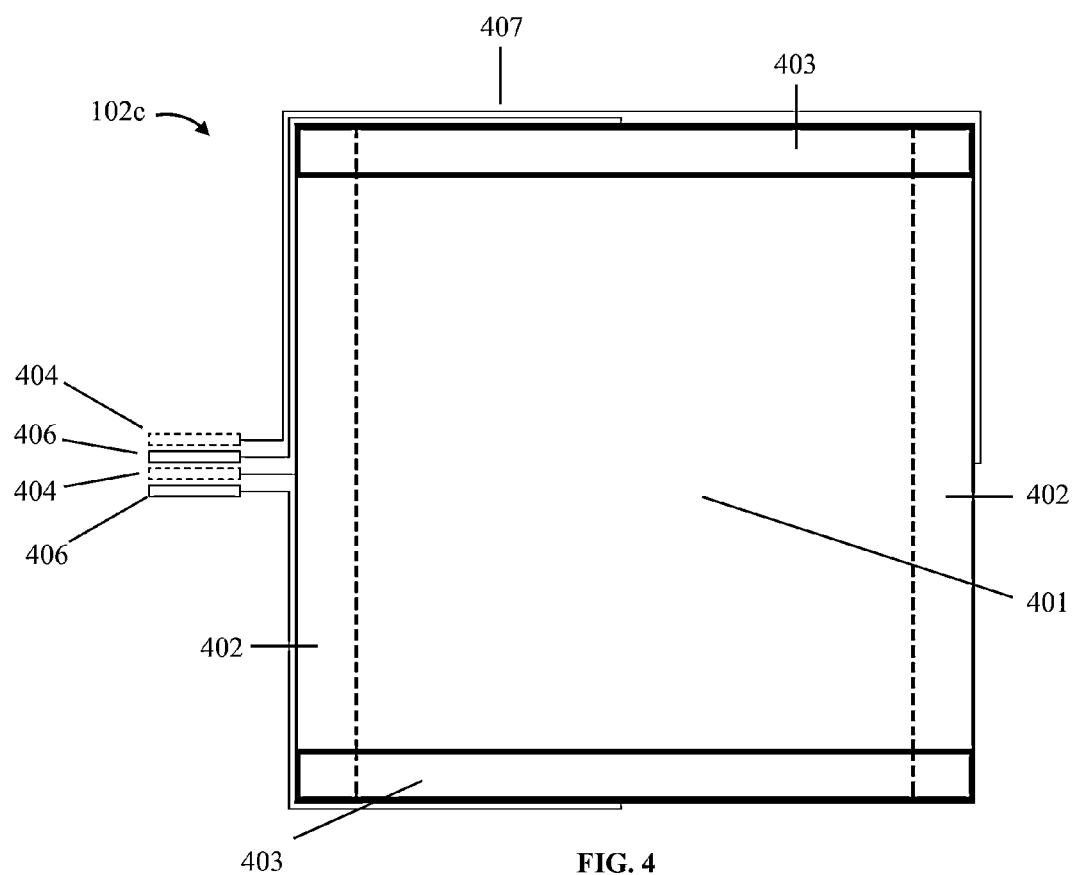
FIG. 4 is a touch screen circuit pattern for a resistive layer of touch screen material.

FIG. 4 is a resistive touch screen circuit pattern 102c that may be disposed on a sheet of material to comprise a resistive layer of touch screen material 101. Generally, such resistive layers of touch screen material are constructed out of two substantially transparent and resistive sheets, for example, coated with ITO, that are bonded together such the two sheets are separated by a small and substantially hollow air gap, for example, bonded together at a plurality of microdots comprising an insulating material. In that case, the substantially hollow air gap is located within boundaries of touch input surface 401. Resistive touch screen circuit pattern 102*c* is a four-wire design that comprises printed bus bars, for example, printed using silver ink: two lower sheet bus bars 402 and two upper sheet bus bars 403. Lower sheet bus bars 402 are in electrical communication with lower sheet terminals 404 and upper sheet bus bars 403 are in electrical communication with upper sheet terminals 406 through traces 407, for example, printed using ITO. When such resistive touch screen materials are operated, a unidirectional voltage gradient is applied to one of the sheets, for example, the lower sheet through lower sheet terminals 404. When the resistive layer of touch screen material is contacted, the substantially hollow air gap between the sheets closes and the sheets contact one another. This contact can be measured as a voltage along the bus bars of one sheet, for example, lower sheet bus bars 402, to determine a first coordinate, and a voltage along the bus bars of the other sheet, for example, upper sheet bus bars 403, to determine a second coordinate. The first and second coordinates may be used to determine the location of a touch input on the layer of touch screen material. If the layer is defective, for example, manufactured such that the upper and lower sheets are electrically shorted before touch screen sensor manufacturing, erroneous touch inputs can be detected.

Figure 5:
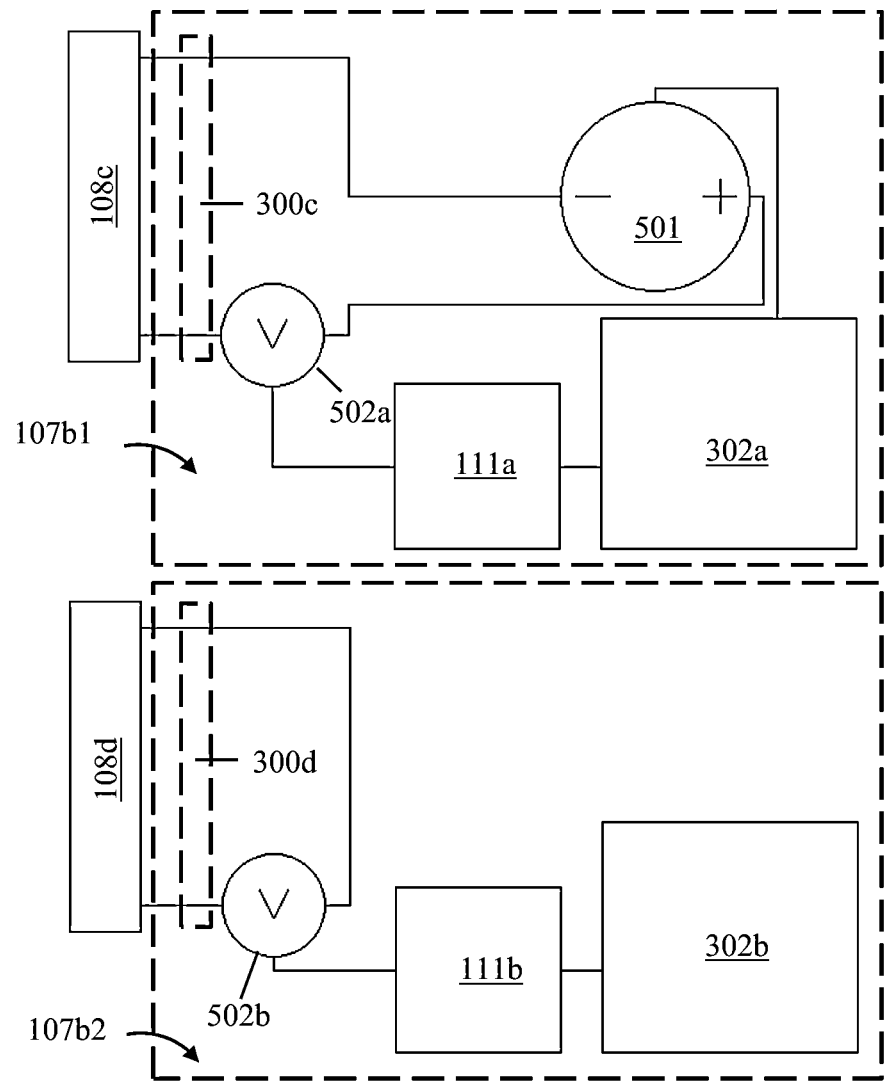
FIG. 5 is an example of impedance measurement circuits of one embodiment of the present test fixtures configured to test the resistive layer of touch screen material of FIG. 4.

Referring now to FIG. 5, due to the two sheet two-sided structure of such resistive layers of touch screen material, embodiments of the present test fixtures designed to test resistive layers of touch screen material which comprise resistive touch screen circuit pattern 102*c* comprise a first and second test bed 103, 104 where each test bed has an electrical connector 108*c*, 108*d*, and an impedance measurement circuit 107*b*1, 107*b*2, respectively. Impedance measurement circuit 107*b*1 may be configured to communicate with either the lower sheet terminals 404 or the upper sheet terminals 406, and impedance measurement circuit 107*b*2 may then be configured to communicate with the terminals (lower sheet terminals 404 or upper sheet terminals 406) not in communication with impedance measurement circuit 107*b*1. By way of example what follows is a detailed description of impedance measurement circuits 107*b*1 and 107*b*2 where impedance measurement circuit 107*b*1 is configured to communicate with upper sheet terminals 406. In the embodiment shown, impedance measurement circuit 107*b*1 comprises circuitry 300*c* configured to place a voltage source 501 into electrical communication with connector 108*c*, and thus the upper sheet terminals 406 of touch screen circuit pattern 102*c*. In the embodiment shown, voltage source 501 may be configured to apply, for example, through electrical communication with control unit 302*a*, a voltage to the upper sheet through upper sheet terminals 406, through traces 407, and to upper sheet bus bars 403. In the embodiment shown, impedance measurement circuit 107*b*1 may further comprise a voltmeter 502*a* configured to measure the voltage across the upper sheet bus bars 403. Additionally, in the embodiment shown, impedance measurement circuit 107*b*1 may further comprise a processor 111*a* in electrical communication with control unit 302*a* and voltmeter 502*a*, where processor 111*a* is configured to measure the electrical impedance across the upper sheet bus bars 403. Impedance measurement circuit 107*b*2 may be substantially similar in structure and operation to impedance measurement circuit 107*b*1, with the primary exceptions that impedance measurement circuit 107*b*2 is configured to be in electrical communication with the lower sheet terminals 404 and thus the lower sheet bus bars 402 and does not include a voltage source. In other embodiments of the present test fixtures configured to test resistive layers of touch screen material, the impedance measurement circuits may only comprise circuitry, for example, circuitry 300*c* and 300*d* respectively, and other components, for example, voltage source 501, voltmeters 502*a* and 502*b*, control units 302*a* and 302*b*, and/or processors 111*a* and 111*b* may be located outside of the impedance measurement circuits, for example, disposed on test beds 103, 104, and/or outside of the test fixture. In such other embodiments, control units 302*a* and 302*b* may comprise one control unit, processors 111*a* and 111*b* may comprise one processor, and processor(s) 111*a* and 111*b* may form an integral part of control unit(s) 302*a* and 302*b*.

Figure 6:
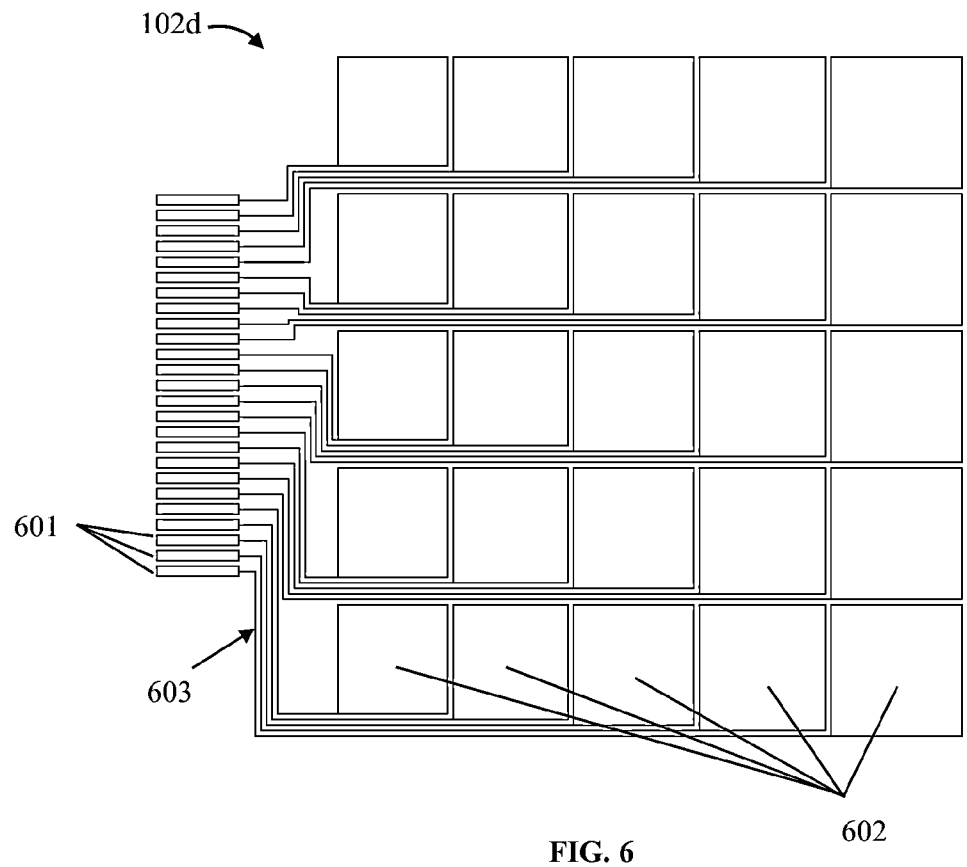
FIG. 6 is a touch screen circuit pattern for a self-capacitive layer of touch screen material.

FIG. 6 is a self-capacitive touch screen circuit pattern 102*d* that can be disposed on a sheet of material 101 to comprise a self-capacitive layer of touch screen material. Self-capacitive touch materials can be constructed by bonding two separate sheets together, with one sheet comprising printed terminals, traces, and rows of elongated electrodes, and the other sheet comprising printed terminals, traces, and columns of elongated electrodes to form a two-sided self-capacitive layer of touch screen material similar to that depicted in FIG. 2B. However, as shown, self-capacitive touch screen materials may also be constructed from a single sheet of insulating material, for example, PET, by printing terminals 601, traces 603, and electrode pads 602 onto the sheet using, for example, ITO, to form a single-sided self-capacitive layer of touch-screen material 101. During operation, a steady state AC signal is applied to each electrode pad 602 (through its corresponding terminal 601). When an object is brought near to or touches the touch screen material, the capacitive load on nearby electrode pads changes. These changes may be detected by a processor as a change in the current applied to those electrode pads, thus indicating the location of the touch. The operating principles of two-sided and single-sided self-capacitive layers of touch screen material are substantially similar, with the primary exception that touch locations for two-sided self-capacitive layers of touch material are determined monitoring the current through row and column electrodes disposed on opposite sides of the layer (a two modal method) rather than pad electrodes (a single modal method) as described for FIG. 6. If the layer of touch screen material is defective (e.g., an electrode is shorted to ground, broken, and/or the like), erroneous touch inputs can be detected and/or valid touch inputs can be ignored.

Figure 7:
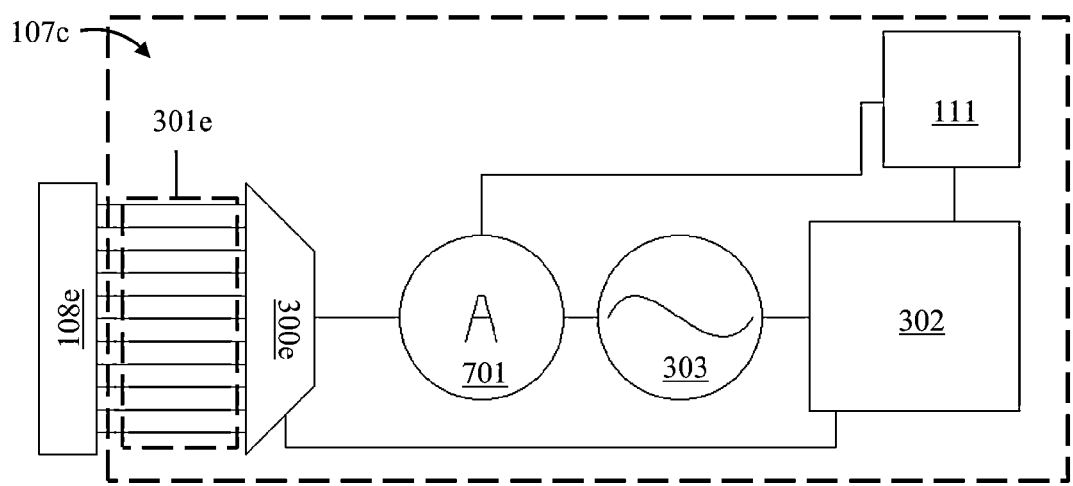
FIG. 7 is an impedance measurement circuit of one embodiment of the present test fixtures configured to test the self-capacitive layer of touch screen material of FIG. 6

Referring now to FIG. 7, embodiments of the present test fixtures designed to test single-sided self-capacitive layers of touch screen material comprising circuit pattern 102*d* comprise a first and second test bed 103, 104 where at least one test bed comprises an electrical connector 108*e* and an impedance measurement circuit 107*c* Measurement circuit 107*c* is configured to communicate with terminals 601 through circuitry 300*e* when the test beds are moved relative to one another to secure the single-sided self-capacitive layer of touch screen material 101 including circuit pattern 102*d*. In the embodiment shown, impedance measurement circuit 107*c* further comprises a multiplexer 301*c* configured, for example, through electrical communication with control unit 302, to select individual electrode pads 602 such that AC signal generator 303 can send an AC signal through each electrode pad. In the embodiment shown, ammeter 701 may then measure the current passing through each electrode pad. Additionally, in the embodiment shown, measurement circuit 107*c* further comprises a processor 111 in electrical communication with control unit 302 and ammeter 701 where processor 111 is configured to measure the impedance of at least one of the electrode pads. In other embodiments configured to test single-sided self-capacitive layers of touch screen material comprising circuit pattern 102b, the impedance measurement circuit may only comprise circuitry, for example, 300e), and other components, for example, multiplexer 301c, ammeter 701, AC signal generator 303, control unit 302 and/or processor 111, may be located outside of the impedance measurement circuit, for example, disposed on test beds 103 and/or 104, or outside of the test fixture. Additionally, in other embodiments, processor 111 may form an integral part of control unit 302. Embodiments of the present test fixtures configured to test two-sided self-capacitive layers of touch material (described briefly above) may be substantially similar to the embodiment described with reference to FIG. 7, with the primary exception that such embodiments comprise two test beds 103,104 where each test bed has an electrical connector, for example, 108e, and an impedance measurement circuit, for example, 107c, such that the test fixture can be in electrical communication with both sides of the two-sided self-capacitive layer of touch material 101.

Figure 8:
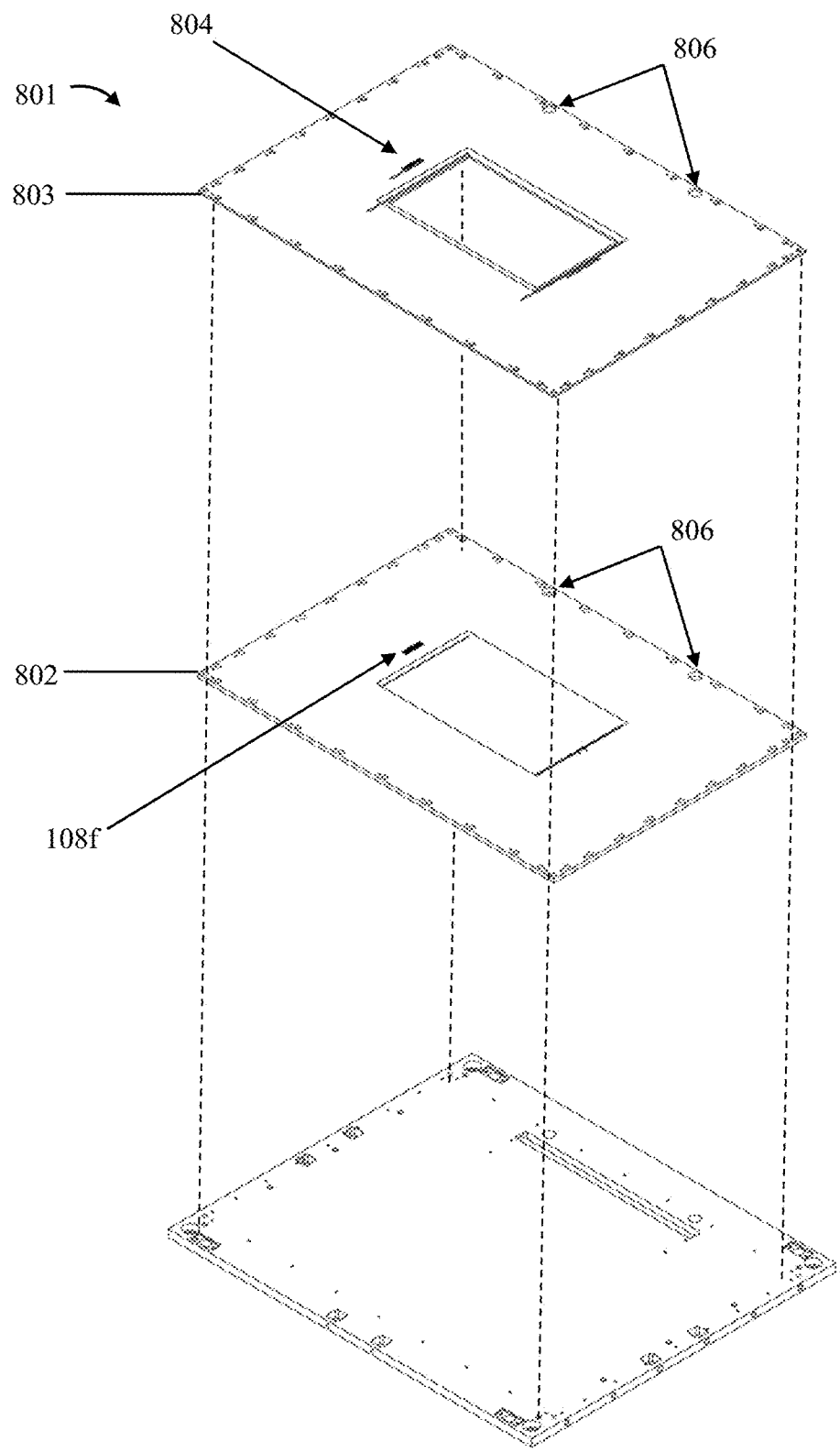
FIG. 8 is an exploded view of one embodiment of a test bed for use in the present test fixtures.

FIG. 8 is a test bed 801 of the present test fixtures suitable for use as test bed 103 or 104. Test bed 801 comprises an impedance measurement circuit, for example, 107a, 107b1, 107b2, or 107c, disposed on contact printed circuit board (PCB) 802 and an electrical connector 108f (for example, 108a, 108b, 108c, 108d, or 108e) configured to be in electrical contact with a layer of touch screen material 101 including touch screen circuit pattern 102a, 102b, 102c, or 102d. In the embodiment shown, test bed 801 further comprises a spacer 803 disposed between test bed 801 and layer 101 such that the test bed does not contact the touch input surface (for example, the junctions 206 and 206a of circuit patterns 102a and 102b, touch input surface 401 of circuit pattern 102c, or electrode pads 602 of circuit pattern 102d, when the layer 101 is secured between the test beds during testing. When the test beds, for example, test bed 801, are brought into contact with the layer of touch screen material 101, while not required in all embodiments of the present test fixtures, it may be desirable to prevent contact with the touch screen circuit patterns 102 of the layer 101. This can prevent the impedance measurement circuit from measuring touch inputs which can be caused in some touch screen circuit patterns (e.g., 102c) by compression between the two test beds, and may prevent any damage to the touch screen circuit pattern 102. However, in other embodiments, particularly test fixtures configured to test self-capacitive layers of touch screen material having self-capacitive touch screen circuit patterns (for example, 102d) spacers (e.g., 803) of the test bed(s) may comprise a flat sheet of conductive material configured to contact the touch screen circuit pattern(s) 102 of layer 101. Through such features, signals generated within the touch screen circuit patterns, for example, self-capacitive signals, during testing may be amplified, facilitating functional testing of such self-capacitive layers of touch screen material. In the embodiment shown, spacer 803 of test bed 801 may be further configured such that electrical connector 108f passes through the spacer, for example, through aperture 804, whereby connector 108f is secured by the spacer and substantially restrained from laterally deflecting under compression by sidewalls of aperture 804. Through such features, when a test bed comprising a spacer (e.g., 801) is brought into contact with the layer of touch screen material, the electrical connector of the test bed is able to communicate with any touch screen circuit patterns on the layer of touch screen material. Additionally, in the embodiment shown, electrical connector 108f may comprise an elastomeric connector constructed out of thin alternating elastomeric layers of conductive and non-conductive layers oriented vertically in the contact direction, such as, for example a Series 5002 Zebra High Performance Silver Connector available from Fujipoly, or a Z-Silver connector available from the Z-Axis Connector Company. Such electrical connectors are capable of making the desired connection between impedance measurement circuit (107, 107a, 107b1, 107b2, or 107c) and touch screen circuit patterns (102, 102a, 102b, 102c, or 102d) on the layer of touch screen material 101 without the need for an exact contact location between the connector and any terminals of the touch screen circuit pattern, for example, even if the electrical connector is shifted slightly, the thin conductive layers will correctly connect any terminals of the circuit pattern with any circuitry of the impedance measurement circuit of the test bed. However, it may be advantageous to secure such elastomeric electrical connectors to ensure that the electrical connectors remain substantially fixed during testing conditions, for example, by restraining any lateral deflection of electrical connector 108f when the test beds are brought into contact with the layer of touch screen material. In the embodiment shown, spacer 803 and contact PCB 802, containing an impedance measurement circuit, are separate components, and may be aligned relative to one another through the insertion of pins in alignment holes 806. Screws and/or a friction fit between alignment holes 806 and pins may ensure that spacer 803 and contact PCB 802 do not move relative to one another during testing. However, in other embodiments, contact PCB 802 may be coupled to spacer 803 in any way which permits the functionality described in this disclosure (for example, through fasteners, interlocking features, and/or the like) such that contact printed circuit board 802 and spacer 803 maintain alignment relative to one another during testing. Additionally, in other embodiments, spacer 803 may form an integral part of the test bed. For example, contact PCB 802 and spacer 803 may be constructed from a single piece of material.

Figure 9A:
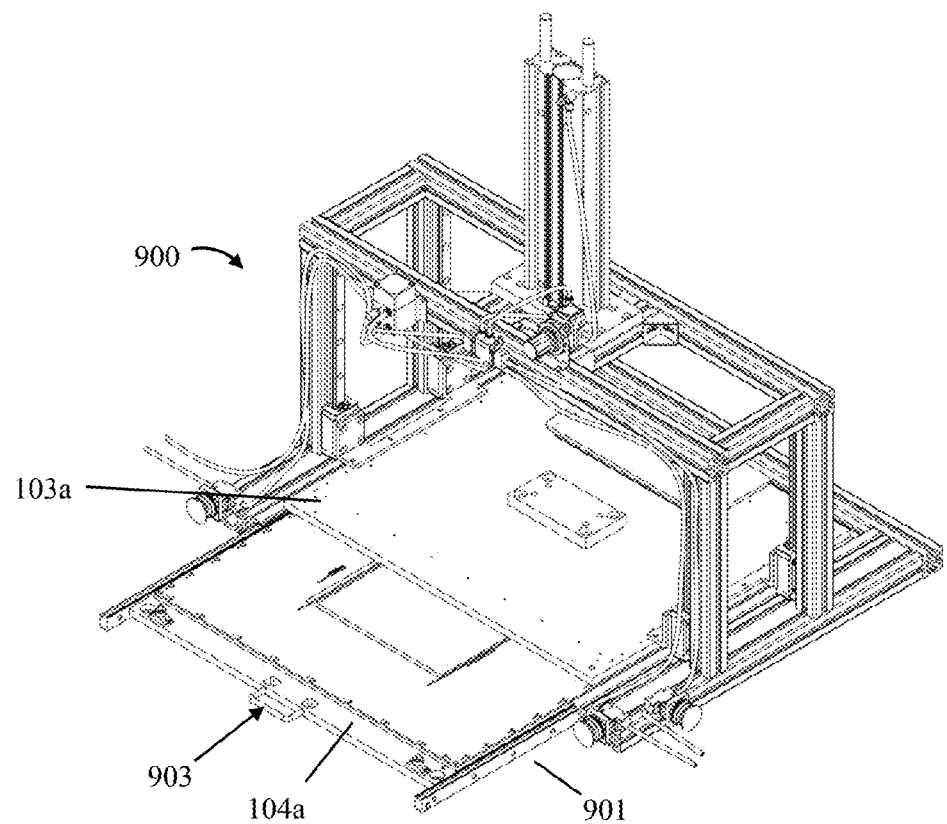
FIG. 9A is one embodiment of the present test fixtures configured to allow test bed changes to test various layers of touch screen material.
Figure 9B:
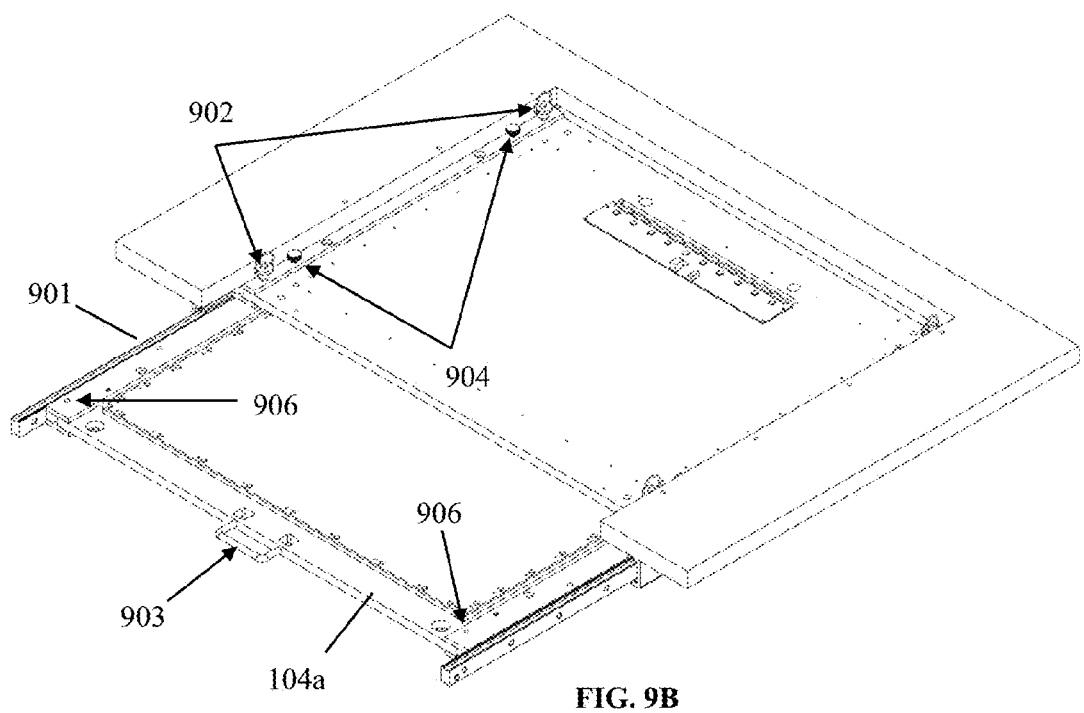
FIG. 9B is a bottom perspective view of the embodiment of FIG. 9A.

Embodiments of the present test fixtures are not limited to the touch screen circuit patterns and/or layers of touch screen material described above. Referring now to FIGS. 9A and 9B, given the variety of layers of touch screen material that can be tested (including, but not limited to, touch screen circuit patterns 102a, 102b, 102c, 102d, and those that may be later developed), some embodiments of the present test fixtures 900 are designed to be modular in nature. In the embodiment shown, test beds 103a and 104a are slidably resealably coupled to test fixture 900 by rails 901 such that test bed 103a and/or 104a may be quickly removed from and inserted into test fixture 900. In other embodiments, test beds 103a, 104a may be releasably coupled to the test fixture through any means which permit the functionality described in this disclosure, including, but not limited to, interlocking features, sliders, and/or the like. Additionally, releasable operation may be facilitated through lubrication, bushings, ball bearings and/or the like. Through such features, these embodiments of the present test fixtures may be configured to test any touch screen circuit patterns (e.g., 102) by inserting appropriate test beds with the corresponding electrical connector(s) and/or impedance measurement circuit(s) as described above. In the embodiment shown, and referring to FIG. 9B, test fixture 900 further comprises latching mechanisms 902 configured to securely and releasably latch test beds inserted into the test fixture and ensure proper alignment of test beds within the test fixture. In the embodiment shown, latching mechanisms 902 comprise spring-loaded quick-release pins configured to releasably secure the test bed(s) into the test fixture. For example, when the test bed(s) are inserted into the test fixture, the quick-release pins may move forward into detents 906 (e.g., recessed areas, holes, and/or the like) to hold the test bed(s) relative to the test fixture in location(s) suitable for testing a layer of touch screen material 101. For further example, when the test bed(s) are to be changed or otherwise removed from the test fixture, the quick-release pins may be released (e.g., by pulling against the spring tension of the quick-release pins to retract the pins from their respective detents 906) to allow removal of the test bed(s) from the test fixture. In other embodiments, the test bed(s) may be releasably secured and/or further secured by different and/or additional latching mechanisms such as fasteners (e.g., thumb screws 904), interlocking features, latches, and/or the like which can be disposed on the test bed(s) and/or test fixture. Additionally, as shown, removable test beds (e.g., 103a and/or 104a) may include a handle 903 to further facilitate removal and insertion of test beds into the test fixture. Through such features, a user could, for example, remove a test bed from the test fixture by releasing any latching mechanism(s) 902, pulling on handle 903, and sliding the test bed from the test fixture by rails 901, insert a different test bed into the test fixture by rails 901, releasably secure the test bed into the test fixture (e.g., through latching mechanisms 902), and further secure the test bed to the test fixture, for example, with thumb screws 904. In some embodiments, rails 901, latching mechanisms 902, handle 903, thumb screws 904 and/or the like are components of the test fixture, and test bed(s) may be mounted or dismounted to such components during installation and removal of test beds, respectively, for example, by fastening a test bed comprising a contact PCB and any spacers to a slide-out tray disposed on the test fixtures.

Figure 10A:
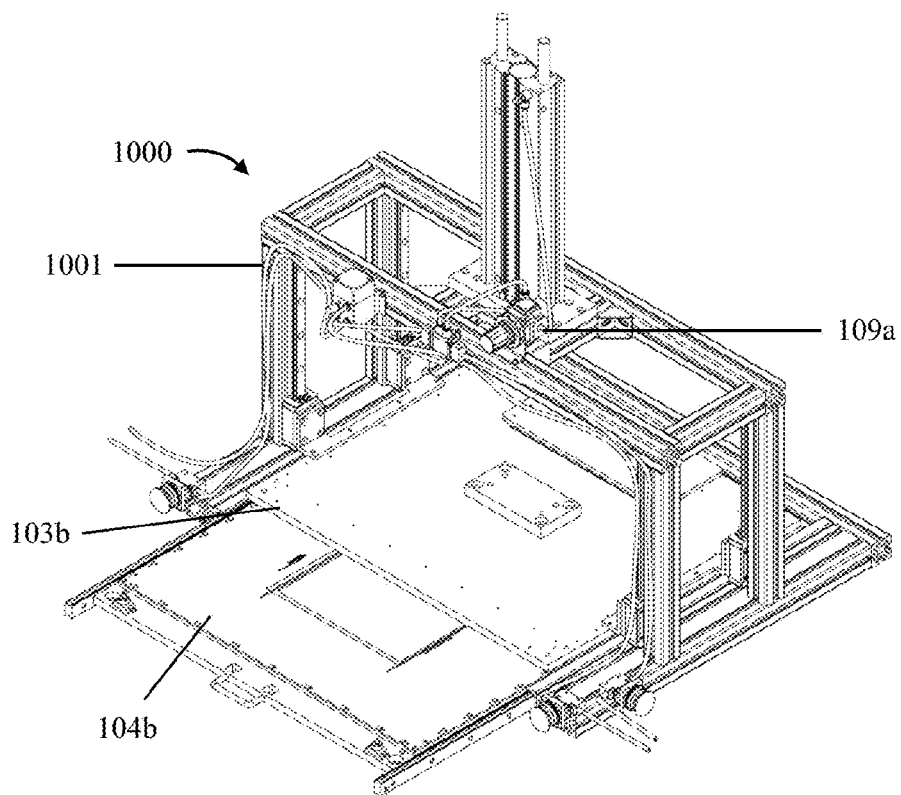
FIG. 10A is one embodiment of the present test fixtures comprising a fluid-driven clamping actuator.
Figure 10B:
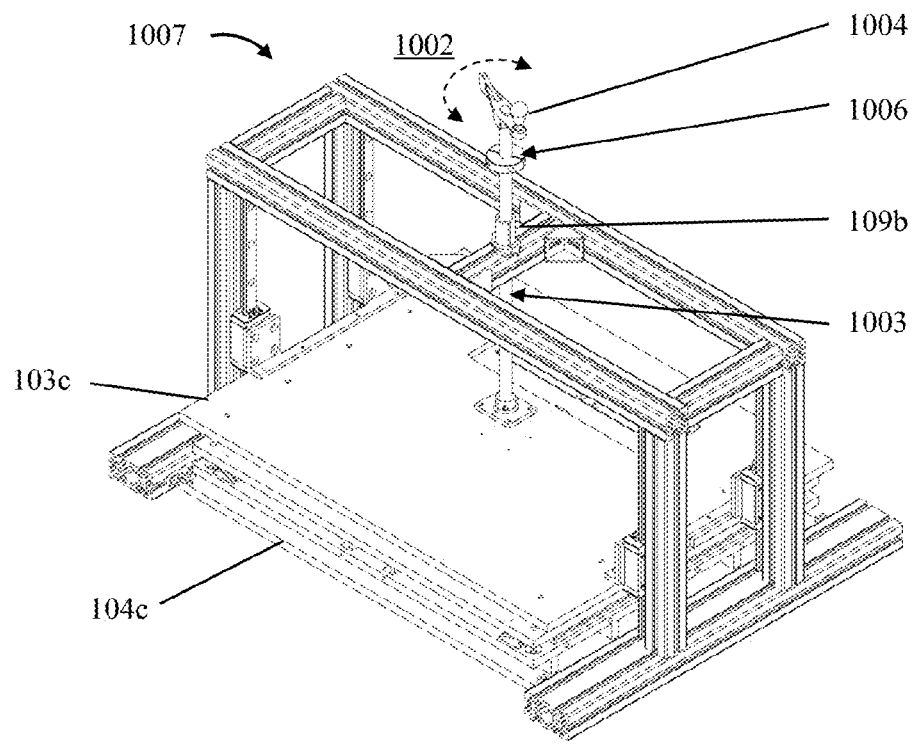
FIG. 10B is one embodiment of the present test fixtures comprising a screw-type clamping actuator.

As described generally above with reference to FIG. 1, some embodiments of the present test fixtures comprise at least one clamping actuator 109 configured to move at least one test bed 103, 104 relative to the other test bed to secure a layer of touch screen material 101 (for example, the mutual capacitive layer touch screen material comprising circuit pattern 102a) between the first and second test beds 103, 104, and to place at least one electrical connector 108 of the test beds 103, 104 in electrical contact with any terminal(s) of the layer. FIGS. 10A and 10B provide non-limiting examples of suitable clamping actuators. FIG. 10A is an embodiment 1000 of the present test fixtures with a fluid-driven clamping actuator 109a. In the embodiment shown, fluid driven clamping actuator 109a moves test bed 103b relative to test bed 104b through fluid pressure supplied by fluid lines 1001, and may be hydraulic with a liquid as the working fluid, or pneumatic with air as the working fluid. In the embodiment shown, fluid-driven clamping actuator 109a is further configured to be in communication with a processor (for example, 111) in order to control test bed movement in order to avoid over pressuring the layer of touch screen material 101 during testing while ensuring adequate contact between electrical connector(s) of the test bed(s) and any terminal(s) of the layer of touch screen material). FIG. 10B depicts another embodiment 1007 of the present test fixtures comprising a screw-type clamping actuator 109b. In the embodiment shown, screw-type clamping actuator 109b moves test bed 103c relative to test bed 104c through rotation of screw 1003 in the directions indicated by arrow 1002. Rotation may be accomplished manually through rotation of handle 1004, or through actuation of a motor (not shown) coupled to screw 1003, for example coupled through a conventional gear, worm gear, or the like. In the embodiment shown, test fixture 1007 further comprises a depth stop 1006, configured to set the minimum distance achievable between test beds 103c and 104c. Depth stop 1006 may prevent screw 1003 from turning past a certain adjustable point. In other embodiments, such depth control may be had through processor (for example, 111) control of the clamping actuator 109, 109a, 109b with position sensors disposed on the test beds and/or the test fixture configured to capture data indicative of test bed location within the test fixture. In yet other embodiments, actuator 109 may comprise any actuator(s) which permit the functionality described in this disclosure, for example, spring actuators, electric actuators, magnetic actuators, or the like, that are capable of moving at least one test bed relative to the other to secure a layer of touch screen material between the test beds.

Figure 11A:
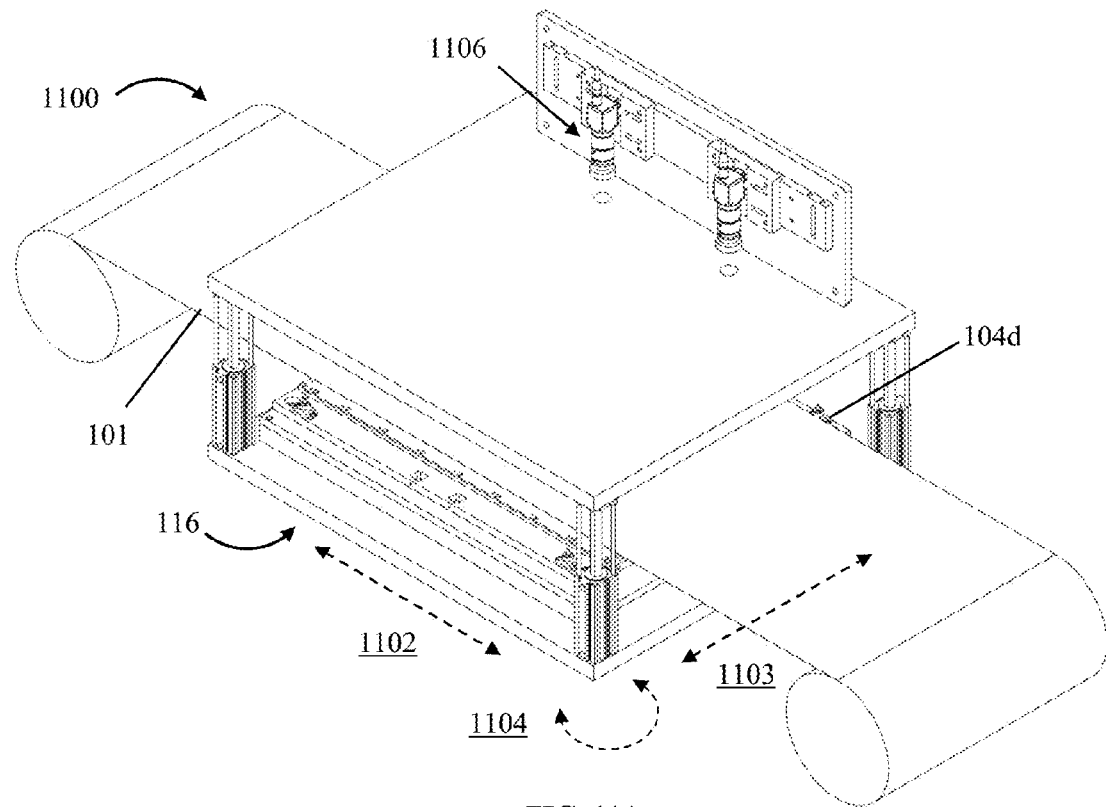
FIG. 11A is one embodiment of the present test fixtures comprising an orientation actuator.
Figure 11B:
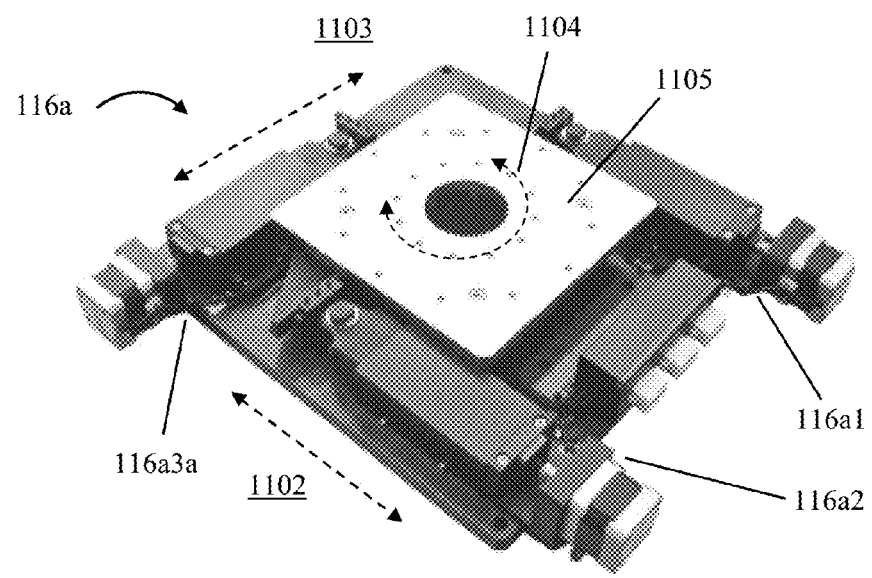
FIG. 11B is an example of an orientation actuator of the embodiment of FIG. 11A.

FIG. 11A is an embodiment 1100 of the present test fixtures comprising at least one orientation actuator 116 configured to move at least one of the test beds, for example test bed 104d, in at least one of a transverse (substantially perpendicular axes 1102 and/or 1103) or rotational (about rotational axis 1104) degree of freedom relative to the layer of touch screen material 101. FIG. 11B depicts an example of a suitable orientation actuator 116a. In the embodiment shown, orientation actuator 116a comprises a plurality of linear actuators (116a1, 116a2, and 116a3) that may act alone and/or together to obtain a desired displacement (e.g., in directions along axes 1102, 1103, and/or rotation about rotational axis 1104). For example, pure translational displacement along axis 1102 may be achieved by simultaneous and equal displacement of linear actuators 116a1 and 116a2, pure translation along axis 1103 may be achieved through displacement of linear actuator 116a3 alone, and pure rotational displacement about rotational axis 1104 may be achieved through simultaneous and equal but opposite displacement of linear actuators 116a1 and 116a2. Any other desired displacements may be achieved through the above linear actuator displacements, alone or in any combination. In the embodiment shown, test fixture 1100 is mounted to base plate 1105 of orientation actuator 116a, for example, with screws and/or other fasteners such that when base plate 1105 moves, the test bed(s) of test fixture 1100 move in a corresponding fashion. In the embodiment shown, test fixture 1100 further comprises at least one sensor 1106 configured to capture data indicative of the orientation of the layer of touch screen material 101 relative to the test fixture 1100. In the embodiment shown, the orientation data comprises images taken by sensor(s) 1106, for example, a camera or cameras, that capture the location of at least one fiducial disposed on the layer of touch screen material 101 and at least one fiducial disposed on the test fixture, for example a printed mark, indentation, or the like. In the embodiment shown, sensors 1106 may communicate with a processor (for example, 111) in order to control the orientation actuator 116a and ensure that the layer of touch screen material is oriented such that when the test beds are brought into contact with the layer, the layer is in a location such that any terminal(s) on any touch screen circuit pattern(s) disposed on the layer are brought into contact with the electrical connector(s) of the test beds. It should also be noted that the fiducial for the test fixture may be a virtual fiducial, with the imaging device (for example, camera) having a substantially fixed position relative to the test fixture. Then, processor 111 would compare the position of a fiducial imaged from layer 101 to a desired virtual position of that fiducial in order to control orientation actuator 116.

Figure 12A:
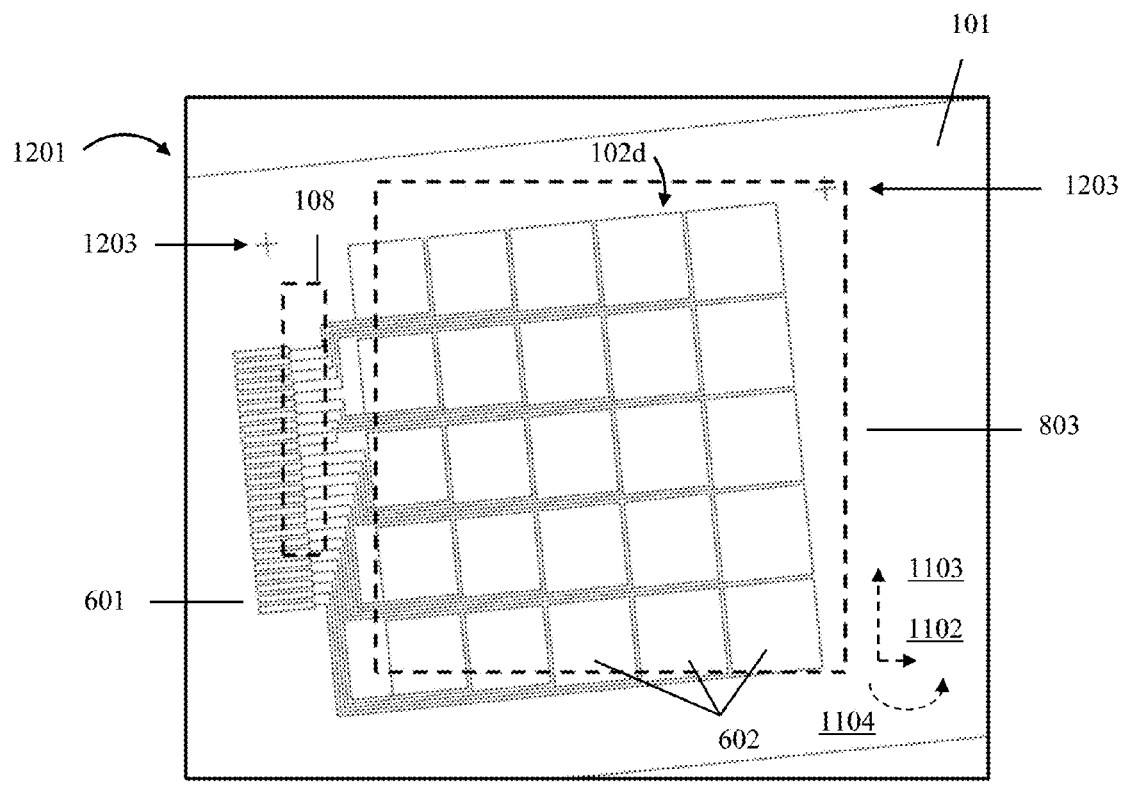
FIGS. 12A and 12B are one method of aligning a layer of touch screen material within one embodiment of the present test fixtures.
Figure 12B:
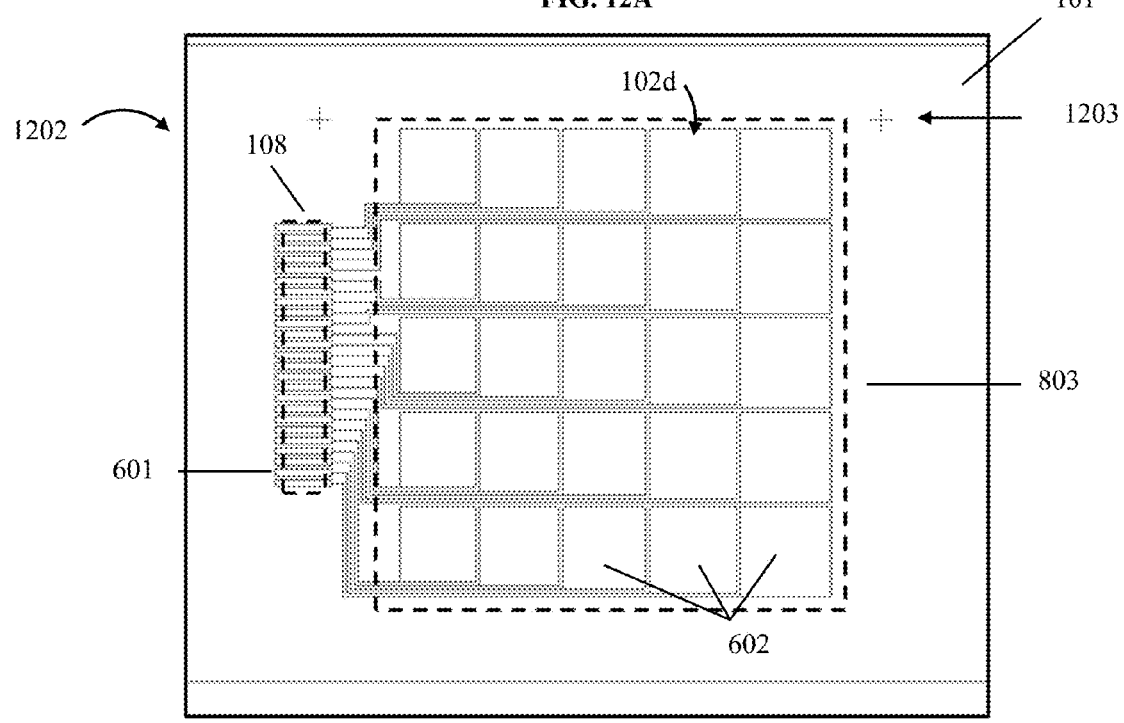

FIGS. 12A and 12B provides an example of the operation of such features. 1201 is a visual representation of data captured by at least one sensor 1106 indicative of the orientation of a layer of touch screen material 101 comprising a touch screen circuit pattern, for example, self-capacitive touch screen circuit pattern 102d as shown, relative to electrical connector 108 and spacer 803 on the test fixture. The location of at least one sensor 1106 relative to the test fixture, as shown by, for example, the orientation of data 1201 and data 1202 relative to electrical connector 108 and spacer 803, may be stored in memory 112, through calibration of the test fixture, or the orientation may be determined through the locating of fiducial(s) disposed on the test bed(s) and/or test fixtures. Layer of touch screen material 101 further comprises at least one fiducial 1203 disposed on the layer. The location of fiducial(s) 1203 relative to any terminal(s) 601 or other touch screen circuit pattern features (e.g., electrode pads 602) can be stored in memory 112 prior to testing. For example, such information may be measured from the layer, provided by the manufacturer of the layer, and/or passed to the test fixture from a circuit pattern printer in a manufacturing setting. Processor 111 may receive data 1201, and determine, for example, through relative location of fiducials 1203 to features of touch screen circuit pattern 102*d* and relative location of test fixture to data 1201, the displacements required to align the test bed with the touch screen circuit pattern under test.

What follows is a description of a suitable fiducial locating algorithm, provided by way of example and not by limitation. In some embodiments of the present test fixtures and/or methods, data 1201 may comprise an image, obtained, for example, by a camera. Some visual-based fiducial locating algorithms work by locating areas of high contrast within an image. In embodiments using such visual-based algorithms for locating fiducials, processor 111 may iteratively scan the pixels in data 1201 to locate selected pixels that have a contrast that is substantially different than that of surrounding pixels for example, substantially brighter or substantially darker. In these embodiments, processor 111 may first and/or additionally convert the image to gray-scale and/or black and white to intensify areas of changing contrast within the image. Processor 111 may then determine the locations of the selected pixels within the image and determine whether the selected pixels define data indicative of a fiducial, for example, by comparing the shape defined by the selected pixels to that of an expected fiducial, which may be stored in memory prior to testing. In these embodiments, the test fixtures may further comprise a light source configured to illuminate the layer of touch screen material to increase the brightness of any fiducial(s) on the layer. The test fixtures and/or test bed(s) may also be painted with, coated with, or constructed out of a light absorbing material to further facilitate fiducial locating. However, the present test fixtures may comprise any fiducial locating hardware, software, method, and/or algorithm that permits the functionality described in this disclosure as long as they have the capability of determining the location of the layer of touch screen material relative to the test beds and/or the test fixture. Additionally, the present test fixtures can be configured to test layers of touch screen material 101 with any number, placement, size, shape of fiducial, for example, cross-shaped, triangular, square, polygonal, circular, or the like.

In the example depicted in FIGS. 12A and 12B, the required displacements are in a negative direction along axes 1102 and 1103, and a positive rotation about rotational axis 1104. The processor 111 may then communicate these required displacements to the orientation actuator 116), which can effectuate the displacements. 1202 is a visual representation of data captured by at least one sensor 1106 indicative of the orientation of the layer after corrective displacement. As shown, electrical connector 108 and spacer 803 are in proper alignment with terminals 601 and electrode pads 602 for testing. If alignment is not proper after initial adjustment, processor 111 can repeat the above steps until proper alignment is obtained and/or report an error code, for example to user interface 113. In other embodiments, any terminal(s) of the touch screen circuit pattern may be printed (e.g., out of a reflective material and/or with a recognizable shape) such that the processor 111 can directly recognize the terminal(s) (e.g., within the data captured by the at least one sensor), thus obviating the need for fiducials 1203.

Figure 13:
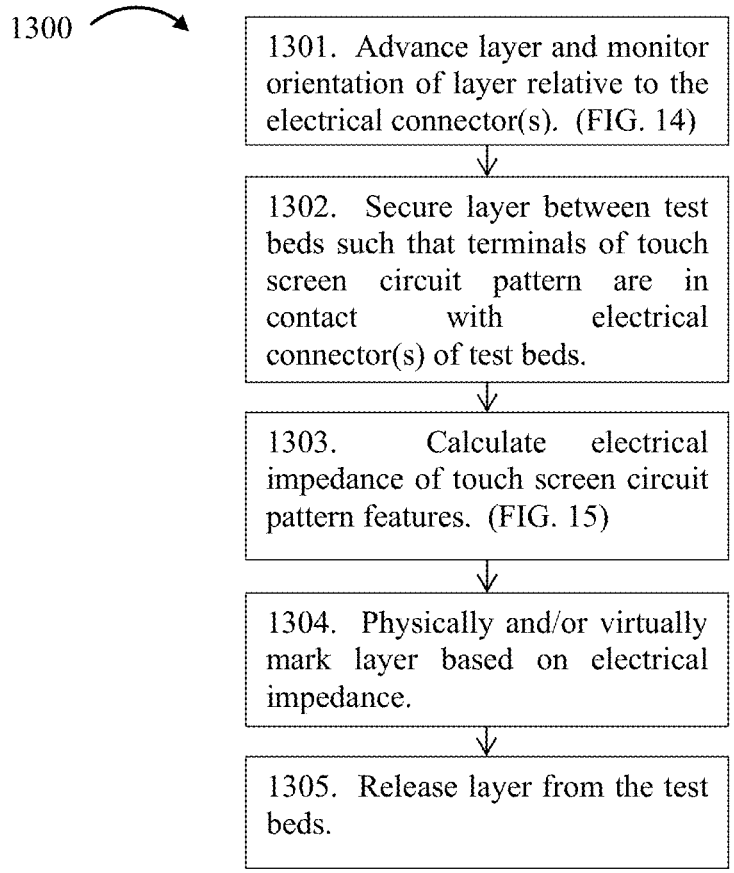
FIGS. 13-15 are flow charts of several embodiments of the present methods to test a layer of touch screen material.
Figure 14:
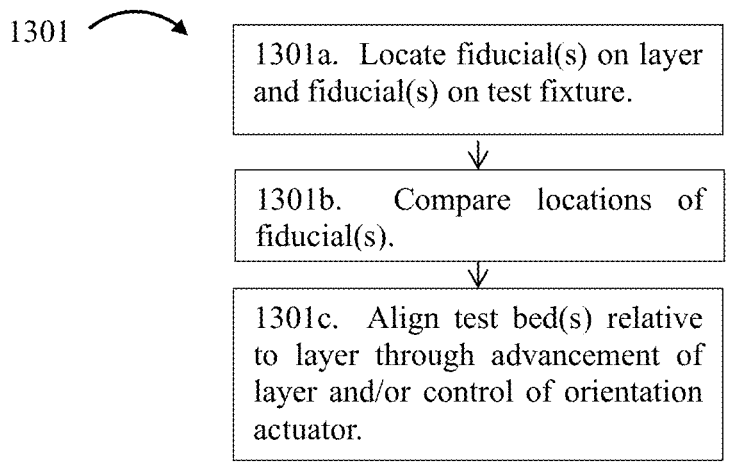
Figure 15:
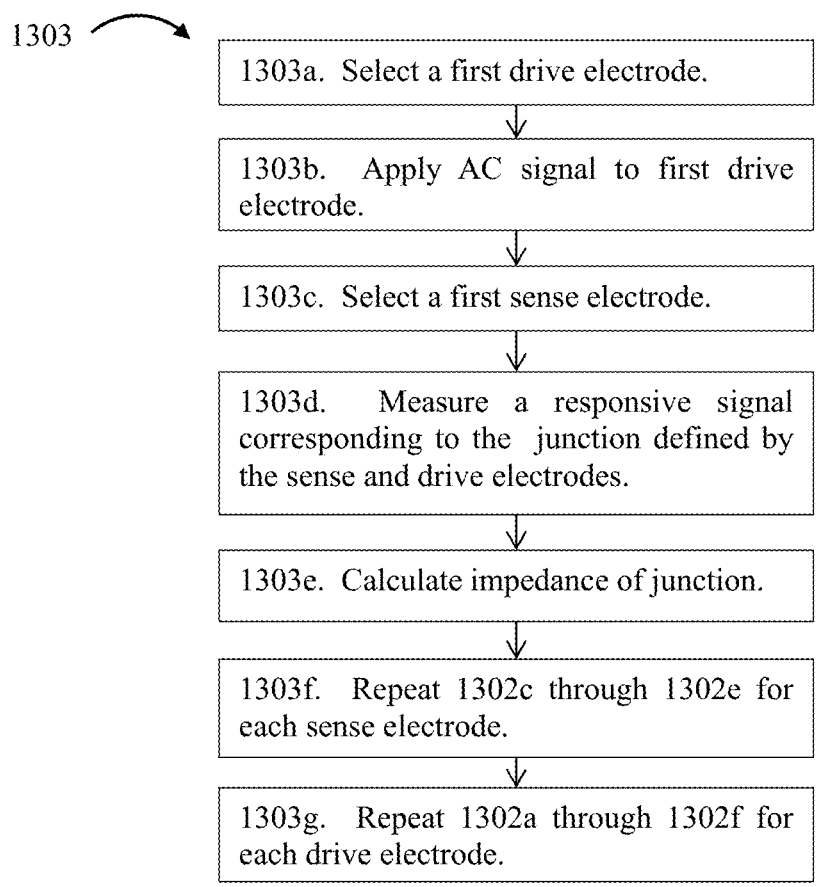

FIGS. 13-15 are flow charts of several embodiments 1300 of the present methods to test a layer of touch screen material. Step 1301 describes a step present in some embodiments of the present methods. In step 1301, shown in more detail in FIG. 14, the orientation of the layer of touch screen material relative to the electrical connector(s) of the test bed(s) may be monitored, for example, with sensor(s) 1106. In one embodiment, at step 1302, the layer of touch screen material 101 is secured between the test beds 103, 104 by moving test bed 103 and/or 104 relative to one another with actuator 109 such that terminals of touch screen circuit pattern (for example, 102*a*, 102*b*, 102*c*, or 102*d*) within the layer 101 are in contact with electrical connector(s) (for example, 108*a*, 108*b*, 108*c*, 108*d*, 108*e*, or 108*f*) of the test beds. At step 1303, the electrical impedance of the features of the touch screen circuit pattern may be calculated through use of a processor 111 and measurement circuits 107*a*, 107*b*1, 107*b*2, or 107*c* as described above. In some embodiments of the present methods, after determining the electrical impedance of touch screen circuit pattern features at step 1303 (shown in more detail in FIG. 15), the layer of touch screen material 101 may then be marked corresponding to the measured impedances 1304. In some embodiments, this marking comprises physically marking the layer (for example, etching with a laser or printing with a printer). In other embodiments, the marking may be virtual (for example, data indicative of the measured impedances of the touch screen circuit pattern features stored in memory 112, communicated through an indicator (for example, 306), or displayed on a user interface (for example, 113)) and may be communicated to further components in a manufacturing setting. For example, the data may be passed to a cutter which is configured to discard sections of a layer of touch screen material with defective touch screen circuit patterns. However, in other embodiments, the marking may be accomplished in any way which permits the functionality described in this disclosure. At step 1305, the layer of touch screen material is then released from the test fixture (e.g., by moving test beds 103 and/or 104 relative to one another and activating any roller(s) supplying the layer to test fixture).

FIG. 14 is a more detailed flow chart of step 1301 showing one embodiment of the present methods to align a layer of touch screen material within one embodiment of the present test fixtures, for example, to monitor an orientation of a layer of touch screen material 101 relative to the electrical connector(s), test bed(s), and/or the test fixture). In the embodiment shown, the monitoring may comprise locating any fiducial(s) on the layer and any fiducial(s) on the test fixture (1301*a*), comparing the locations of the fiducials (1301*b*), for example, with processor 111 in communication with sensors 1106, and aligning the test bed(s) relative to the layer through advancement of the layer (for example if disposed on roller(s)) and/or control of orientation actuator 116 (1301*c*).

FIG. 15 is a more detailed flow chart of step 1301 showing one embodiment of the present methods to test the impedance of circuit pattern features of a layer of touch screen material. Method 1303 represents a non-limiting example of the present methods to test a layer of touch screen material 101 having a touch screen circuit pattern 102 with terminals coupled to capacitive junctions. A first drive electrode may be selected (1303*a*) (for example with multiplexer 301*a* in communication with control unit 302). Next, an AC signal may be applied to the first drive electrode (1303b) (for example, through AC signal generator 303). At 1303c, a first sense electrode may be selected (e.g., with multiplexer 301b in communication with control unit 302). Then a responsive signal with each sense electrode generated through capacitive coupling may be measured which corresponds to the junction defined by the sense and drive electrodes (1303d) (e.g., with ADC 304 in communication with processor 111 and/or control unit 302). With the responsive signal, the impedance of the junction may be calculated (1303e) (for example, by processor 111). Steps 1303c through 1303e are then repeated for each sense electrode 1303f by selecting the individually addressable sense electrodes with multiplexer 301b. Finally, steps 1303a through 1303f may be repeated for each drive electrode (1303g), thus determining the impedance of each capacitive junction in a mutual capacitive touch screen circuit pattern (e.g., 102a or 102b) of a mutual capacitive layer of touch screen material.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A test fixture for testing a layer of capacitive touch screen material having terminals coupled to capacitive junctions, the test fixture comprising:
   first and second test beds moveable relative to each other, at least one test bed including an impedance measurement circuit coupled to at least one electrical connector;
   at least one clamping actuator configured to move at least one test bed relative to the other test bed to secure a layer of capacitive touch screen material having terminals coupled to capacitive junctions between the first and second test beds and to place the at least one electrical connector in electrical contact with the terminals;
   the impedance measurement circuit operable to test an electrical impedance of at least one junction of the layer when the layer is secured between the test beds.

2. The test fixture of claim 1, the impedance measurement circuit comprising a processor programmed to determine impedance.

3. The test fixture of claim 1, further comprising at least one orientation actuator configured to move at least one test bed in at least one of a transverse or rotational degree of freedom relative to the layer.

4. The test fixture of claim 1, at least one test bed comprising a spacer configured to prevent contact with the junctions of the layer when the layer is secured between the test beds.

5. The test fixture of claim 4, the spacer further comprising an aperture configured to secure an electrical connector and substantially restrain the electrical connector from laterally deflecting when the layer is secured between the test beds.

6. The test fixture of claim 1, at least one test bed comprising a spacer comprising a conductive material, the spacer configured to contact the junctions of the layer when the layer is secured between the test beds.

7. The test fixture of claim 1, the at least one electrical connector comprising an elastomeric electrical connector.

8. The test fixture of claim 3, further comprising at least one sensor configured to capture data indicative of the orientation of the layer relative to the test fixture and to control the at least one orientation actuator to align the test fixture with the layer.

9. The test fixture of claim 8, where the at least one sensor comprises a camera.

10. The test fixture of claim 1, comprising:
    apparatus configured to allow removal and replacement of at least one test bed; and
    at least one latch configured to releasably secure the at least one test bed within the test fixture.

11. A method for testing a layer of capacitive touch screen material having terminals coupled to capacitive junctions, comprising:
    securing the layer between first and second test beds, at least one test bed comprising an impedance measurement circuit and an electrical connector, such that the terminals are in electrical contact with the electrical connector of the at least one test bed;
    calculating, with a processor, an electrical impedance of at least one junction of the layer; and
    releasing the layer from the test beds.

12. The method of claim 11, further comprising monitoring an orientation of the layer relative to the electrical connector of the at least one test bed.

13. The method of claim 12, the monitoring step comprising:
    locating a position of a first fiducial disposed on the layer;
    locating a position of a second fiducial disposed on the test fixture; and
    comparing the positions of the first and second fiducials.

14. The method of claim 13, further comprising adjusting an orientation of at least one test bed relative to the layer based on the comparison of the positions of the first and second fiducials.

15. The method of claim 13, further comprising controlling advancement of the layer based on the comparison of the positions of the first and second fiducials.

16. The method of claim 11, further comprising marking the layer based on the electrical impedance of the at least one junction of the layer.

17. The method of claim 11, further comprising storing, in a memory, data indicative of the electrical impedance of the at least one junction of the layer.

18. The method of claim 11,
the junctions of the layer being defined by a plurality of elongated drive and sense electrodes; and
the calculating step comprising:
- (a) selecting a first drive electrode of the layer;
- (b) applying an alternating current signal to the first drive electrode;
- (c) selecting a first sense electrode;
- (d) measuring a responsive signal corresponding to the junction defined by the first drive electrode and the first sense electrode;
- (e) calculating an electrical impedance of the junction based on the responsive signal;
- (f) repeating steps (c) through (e) until each sense electrode has been selected; and
- (g) repeating steps (a) through (f) until each drive electrode has been selected.

19. An apparatus for testing a layer of capacitive touch screen material, the apparatus comprising:
- a test bed including a measurement circuit and a connector, the measurement circuit configured to be in releasable electrical contact with a layer of a capacitive touch screen material via the connector, the layer having terminals coupled to capacitive junctions; and
- a spacer configured to be disposed between the test bed and the layer such that the test bed does not contact the capacitive junctions of the layer when the measurement circuit is in electrical contact with the layer.

20. The test bed of claim 19, the spacer configured such that the connector passes through the spacer, the connector being secured by the spacer and substantially restrained from laterally deflecting under compression.

\* \* \* \* \*